US011434524B2

(12) United States Patent
Ramachandran Iyer et al.

(10) Patent No.: US 11,434,524 B2
(45) Date of Patent: Sep. 6, 2022

(54) METHODS FOR DETERMINING A LOCATION OF AN ANALYTE IN A BIOLOGICAL SAMPLE

(71) Applicant: 10x Genomics, Inc., Pleasanton, CA (US)

(72) Inventors: Eswar Prasad Ramachandran Iyer, Pleasanton, CA (US); Zachary Bent, Pleasanton, CA (US); Yifeng Yin, Pleasanton, CA (US); Eileen Dalin, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/565,081

(22) Filed: Dec. 29, 2021

(65) Prior Publication Data

US 2022/0119869 A1   Apr. 21, 2022

Related U.S. Application Data

(63) Continuation of application No. PCT/US2021/036557, filed on Jun. 9, 2021.

(60) Provisional application No. 63/037,458, filed on Jun. 10, 2020.

(51) Int. Cl.
*C12Q 1/6837* (2018.01)
*C12Q 1/6841* (2018.01)

(52) U.S. Cl.
CPC ......... *C12Q 1/6837* (2013.01); *C12Q 1/6841* (2013.01)

(58) Field of Classification Search
CPC ...... C12Q 1/68; C12Q 1/6837; C12Q 1/6841; C12Q 1/6869
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,136,592 A | 10/2000 | Leighton |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,300,063 B1 | 10/2001 | Lipshutz et al. |
| 6,309,824 B1 | 10/2001 | Drmanac |
| 6,344,316 B1 | 2/2002 | Lockhart |
| 6,355,431 B1 | 3/2002 | Chee |

(Continued)

FOREIGN PATENT DOCUMENTS

| | | |
|---|---|---|
| CN | 1680604 | 10/2005 |
| CN | 101221182 | 7/2008 |

(Continued)

OTHER PUBLICATIONS

U.S. Appl. No. 60/416,118, filed Oct. 3, 2002, Fan et al.
U.S. Appl. No. 61/267,363, filed Dec. 7, 2009, Fan et al.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.

(Continued)

*Primary Examiner* — Ethan C Whisenant
(74) *Attorney, Agent, or Firm* — Fish & Richardson P.C.

(57) ABSTRACT

Provided herein are methods of determining a location of a target analyte in a non-permeabilized biological sample that include the use of a blocking probe.

30 Claims, 6 Drawing Sheets

(56) References Cited

U.S. PATENT DOCUMENTS

| | | |
|---|---|---|
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,914,981 B2 | 3/2011 | Barany et al. |
| 7,955,794 B2 | 6/2011 | Shen et al. |
| 7,960,119 B2 | 6/2011 | Chee |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,278,034 B2 | 10/2012 | Muraca |
| 8,288,103 B2 | 10/2012 | Oliphant |
| 8,383,338 B2 | 2/2013 | Kitzman |
| 8,460,865 B2 | 6/2013 | Chee |
| 8,481,257 B2 | 7/2013 | Van Eijk |
| 8,481,292 B2 | 7/2013 | Casbon |
| 8,481,698 B2 | 7/2013 | Lieberman et al. |
| 8,507,204 B2 | 8/2013 | Pierce et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 9,005,891 B2 | 4/2015 | Sinicropi et al. |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,376,716 B2 | 6/2016 | Van Eijk |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,657,335 B2 | 5/2017 | Van Eijk |
| 9,670,542 B2 | 6/2017 | Van Eijk |
| 9,702,004 B2 | 7/2017 | Van Eijk |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,273,541 B2 | 4/2019 | Hindson et al. |
| 10,472,669 B2 | 11/2019 | Chee |

(56) References Cited

U.S. PATENT DOCUMENTS

| | | |
|---|---|---|
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,633,648 B2 | 4/2020 | Seelig et al. |
| 10,724,078 B2 | 7/2020 | Van Driel et al. |
| 10,774,372 B2 | 9/2020 | Chee et al. |
| 10,774,374 B2 | 9/2020 | Frisen et al. |
| 10,787,701 B2 | 9/2020 | Chee |
| 10,829,803 B2 | 11/2020 | Terbrueggen et al. |
| 10,913,975 B2 | 2/2021 | So et al. |
| 10,914,730 B2 | 2/2021 | Chee et al. |
| 10,927,403 B2 | 2/2021 | Chee et al. |
| 11,008,607 B2 | 5/2021 | Chee |
| 11,046,996 B1 | 6/2021 | Chee et al. |
| 11,067,567 B2 | 7/2021 | Chee |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,359,228 B2 | 6/2022 | Chee et al. |
| 11,365,442 B2 | 6/2022 | Chee |
| 11,371,086 B2 | 6/2022 | Chee |
| 2001/0055764 A1 | 12/2001 | Empendocles et al. |
| 2002/0040275 A1 | 4/2002 | Cravatt |
| 2002/0055100 A1 | 5/2002 | Kawashima |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0257284 A1* | 11/2005 | Nakajima .......... C12N 15/8274 800/278 |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1* | 4/2007 | Boyd .................. C12Q 1/6827 435/6.16 |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1* | 7/2007 | Luo .................... C12Q 1/6844 435/6.12 |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0233802 A1 | 9/2009 | Bignell et al. |
| 2009/0253581 A1 | 10/2009 | Van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1* | 10/2010 | May .................... C12Q 1/686 435/91.5 |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Illumina |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |

(56) References Cited

U.S. PATENT DOCUMENTS

| | | |
|---|---|---|
| 2013/0005594 A1 | 1/2013 | Terbreggen et al. |
| 2013/0005600 A1 | 1/2013 | Olek |
| 2013/0035239 A1 | 2/2013 | Kong et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0274731 A1 | 9/2014 | Raymond et al. |
| 2014/0323330 A1 | 10/2014 | Glezer et al. |
| 2014/0342921 A1 | 11/2014 | Weiner |
| 2015/0000854 A1 | 1/2015 | Gann-Fetter et al. |
| 2015/0344942 A1* | 12/2015 | Frisen ............... C12Q 1/6841 506/30 |
| 2016/0019337 A1 | 1/2016 | Roberts et al. |
| 2016/0024576 A1 | 1/2016 | Chee |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0333403 A1 | 11/2016 | Chee |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335410 A1 | 11/2017 | Driscoll et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0094316 A1 | 4/2018 | Oliphant et al. |
| 2018/0112261 A1 | 4/2018 | Van Driel et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0237864 A1 | 8/2018 | Imler et al. |
| 2018/0245142 A1* | 8/2018 | So .................. C12Q 1/6816 |
| 2018/0247017 A1 | 8/2018 | van Eijk et al. |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2019/0017106 A1* | 1/2019 | Frisen ............... C12Q 1/6844 |
| 2019/0055594 A1 | 2/2019 | Samusik et al. |
| 2019/0085383 A1 | 3/2019 | Church et al. |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0330617 A1 | 10/2019 | Church et al. |
| 2019/0367969 A1 | 12/2019 | Belhocine et al. |
| 2020/0010891 A1 | 1/2020 | Beechem et al. |
| 2020/0024641 A1 | 1/2020 | Nolan et al. |
| 2020/0048690 A1 | 2/2020 | Chee |
| 2020/0063195 A1 | 2/2020 | Chee |
| 2020/0063196 A1 | 2/2020 | Chee |
| 2020/0080136 A1 | 3/2020 | Zhang et al. |
| 2020/0109443 A1 | 4/2020 | Chee |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1* | 12/2020 | Schnall-Levin ...... C12Q 1/6874 |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1* | 10/2021 | Lucero ............... C12Q 1/6874 |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1* | 1/2022 | Ramachandran Iyer .................... C12Q 1/6841 |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |

(56) References Cited

U.S. PATENT DOCUMENTS

| | | | |
|---|---|---|---|
| 2022/0090175 | A1 | 3/2022 | Uytingco et al. |
| 2022/0090181 | A1 | 3/2022 | Gallant et al. |
| 2022/0098576 | A1 | 3/2022 | Dadhwal |
| 2022/0098661 | A1 | 3/2022 | Chew et al. |
| 2022/0106632 | A1 | 4/2022 | Galonska et al. |
| 2022/0106633 | A1 | 4/2022 | Engblom et al. |
| 2022/0112486 | A1 | 4/2022 | Ramachandran Iyer et al. |
| 2022/0112545 | A1 | 4/2022 | Chee |
| 2022/0127659 | A1 | 4/2022 | Frisen et al. |
| 2022/0127666 | A1 | 4/2022 | Katiraee et al. |
| 2022/0127672 | A1 | 4/2022 | Stoeckius |
| 2022/0145361 | A1 | 5/2022 | Frenz et al. |
| 2022/0154255 | A1 | 5/2022 | Chee et al. |
| 2022/0170083 | A1 | 6/2022 | Khaled et al. |
| 2022/0195422 | A1 | 6/2022 | Gallant et al. |
| 2022/0195505 | A1 | 6/2022 | Frisen et al. |
| 2022/0196644 | A1 | 6/2022 | Chee |
| 2022/0213526 | A1 | 7/2022 | Frisen et al. |

FOREIGN PATENT DOCUMENTS

| | | |
|---|---|---|
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1999/044062 | 9/1999 |
| WO | WO 1999/044063 | 9/1999 |
| WO | WO 2000/17390 | 3/2000 |
| WO | WO 2001/06012 | 1/2001 |
| WO | WO 2001/009363 | 2/2001 |
| WO | WO 2001/042796 | 6/2001 |
| WO | WO 2001/090415 | 11/2001 |
| WO | WO 2001/096608 | 12/2001 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2009/032167 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2011/008502 | 1/2011 |
| WO | WO 2011/062933 | 5/2011 |
| WO | WO 2011/068088 | 6/2011 |
| WO | WO 2012/049316 | 4/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2015/161173 | 10/2015 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/124101 | 7/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/045181 | 3/2018 |
| WO | WO 2018/064640 | 4/2018 |
| WO | WO 2018/085599 | 5/2018 |
| WO | WO 2018/091676 | 5/2018 |
| WO | WO 2018/136856 | 7/2018 |
| WO | WO 2018/144582 | 8/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/112604 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/176788 | 9/2020 |
| WO | WO 2020/190509 | 9/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/091611 | 5/2021 |

(56) References Cited

FOREIGN PATENT DOCUMENTS

| | | |
|---|---|---|
| WO | WO 2021/092433 | 5/2021 |
| WO | WO 2021/097255 | 5/2021 |
| WO | WO 2021/119320 | 6/2021 |
| WO | WO 2021/133849 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/087273 | 4/2022 |
| WO | WO 2022/098810 | 5/2022 |
| WO | WO 2022/099037 | 5/2022 |
| WO | WO 2022/109181 | 5/2022 |

OTHER PUBLICATIONS

[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cHl7rEk0UXwdl9It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cHl7rEk0UXwdl9It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles vims mRNA from a crude cell lysate," Anal. Biochem., 1990, 189(1):40-50.
Allawi et al., "Thermodynamics and NMR of Internal G·T Mismatches in DNA," Biochemistry, 1996, 36(34):10581-10594.
Andresen et al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buemostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.

(56) References Cited

OTHER PUBLICATIONS

Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Expansionmicroscopy," Science, 2015, 347(6221):543-548.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "µCB-seq: microfluidic cell barcoding and sequencing for high-resolution imaging and sequencing of single cells," Lab Chip, Nov. 2020, 20(21):3899-3913.
Chrisey et al., "Covalent attachment of synthetic DNA to self-assembled monolayer films," Nucleic Acids Res., Aug. 1996, 24(15):3031-9.
Constantine et al., "Use of genechip high-density oligonucleotide arrays for gene expression monitoring," Life Sceience News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cujec et al., "Selection of v-abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.

Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag-protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy", BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.

(56) References Cited

OTHER PUBLICATIONS

Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hahnke et al., "Striptease on glass: validation of an improved stripping procedure for in situ microarrays," J Biotechnol., Jan. 2007, 128(1):1-13.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hu et al., "High reproducibility using sodium hydroxide-stripped long oligonucleotide DNA microarrays," Biotechniques, Jan. 2005, 38(1):121-4.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS One, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Kurz et al., "cDNA—protein fusions: covalent protein-gene conjugates for the in vitro selection of peptides and proteins," ChemBioChem., 2001, 2(9):666-72.
Kwok, "High-throughput genotyping assay approaches," Pharmocogenomics, Febmary 2000, 1(1):95-100.
Lage et al., "Whole genome analysis of genetic alterations in small DNA samples using hyperbranched strand displacement amplification and array-CGH," Genome Research, 2003, 13(2):294-307.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lovatt et al., "Transcriptome in vivo analysis (TIVA) of spatially defined single cells in live tissue," Nature Methods, 2013, 11(2):190-196.

(56) References Cited

OTHER PUBLICATIONS

Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.

Lundberg et al., "High-fidelity amplification using a thermostable DNA polymerase isolated from Pyrococcus furiosus," Gene, 1991, 108(1):1-6.

Lundberg et al., "Homogeneous antibody-based proximity extension assays provide sensitive and specific detection of low-abundant proteins in human blood," Nucleic Acids Res., 2011, 39(15):e102, 8 pages.

Lundberg et al., "Multiplexed homogeneous proximity ligation assays for high-throughput protein biomarker research in serological material," Mol Cell Proteomics, 2011, 10(4):M110.004978, 11 pages.

Lundin et al., "Increased throughput by parallelization of library preparation for massive sequencing," PLoS One, Apr. 2010, 5(4):e10029, 7 pages.

Lyck et al., "Immunohistochemical markers for quantitative studies of neurons and glia in human neocortex," J Histochem Cytochem, 2008, 56(3):201-21.

MacBeath et al., "Printing proteins as microarrays for high-throughput function determination," Science, Sep. 2000, 289(5485):1760-1763.

MacIntyre, "Unmasking antigens for immunohistochemistry.," Br J Biomed Sci., 2001, 58(3):190-6.

Marx, "Method of the Year: spatially resolved transcriptomics," Nature Methods, 2021, 18(1):9-14.

McCloskey et al., "Encoding PCR products with batch-stamps and barcodes," Biochem. Genet., 2007, 45(11-12):761-767.

Meers et al., "Improved CUT&RUN chromatin profiling tools," Elife, Jun. 2019, 8:e46314, 16 pages.

Merritt et al., "Multiplex digital spatial profiling of proteins and RNA in fixed tissue," Nat Biotechnol, May 2020, 38(5):586-599.

Metzker, "Sequencing technologies—the next generation," Nature Reviews Genetics, 2010, 11(1):31-46.

Miele et al., "Mapping cis- and trans-chromatin interaction networks using chromosome conformation capture (3C)," Methods Mol Biol., 2009, 464:105-21.

Miller et al., "Basic concepts of microarrays and potential applications in clinical microbiology," Clinical Microbiology Reviews, 2009, 22(4):611-633.

Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.

Mizusawa et al., "A bacteriophage lambda vector for cloning with BamHI and Sau3A," Gene, 1982, 20(3):317-322.

Morlan et al., "Selective depletion of rRNA enables whole transcriptome profiling of archival fixed tissue," PLoS One, Aug. 2012, 7(8):e42882, 8 pages.

Motea et al., "Terminal deoxynucleotidyl transferase: the story of a misguided DNA polymerase," Biochim Biophys Acta., May 2010, 1804(5):1151-66.

Nandakumar et al., "How an RNA Ligase Discriminates RNA versus DNA Damage," Molecular Cell, 2004, 16:211-221.

Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Nikiforov et al., "The use of 96-well polystyrene plates for DNA hybridization-based assays: an evaluation of different approaches to oligonucleotide immobilization," Anal Biochem, May 1995, 227(1):201-9.

Niklas et al., "Selective permeabilization for the high-throughput measurement of compartmented enzyme activities in mammalian cells," Anal Biochem, Sep. 2011, 416(2):218-27.

Nowak et al., "Entering the Postgenome Era," Science, 1995, 270(5235):368-71.

Ohtsubo et al., "Bacterial insertion sequences," Curr Top Microbiol Immunol., 1996, 204:1-26.

Pandey et al., "Inhibition of terminal deoxynucleotidyl transferase by adenine dinucleotides. Unique inhibitory action of Ap5A," FEBS Lett., Mar. 1987, 213(1):204-8.

Park et al., "Single cell trapping in larger micro wells capable of supporting cell spreading and proliferation," Microfluid Nanofluid, 2010, 8:263-268.

PCT International Search Report and Written Opinion in International Appln. No. PCT/US2021/036557, dated Sep. 16, 2021, 12 pages.

Pellestor et al., "The peptide nucleic acids (PNAs), powerful tools for molecular genetics and cytogenetics," Eur J Hum Genet., Sep. 2004, 12(9):694-700.

Pemov et al., "DNA analysis with multiplex microarray-enhanced PCR," Nucl. Acids Res., Jan. 2005, 33(2):e11, 9 pages.

Perler et al., "Intervening sequences in an Archaea DNA polymerase gen," Proc Natl Acad Sci USA, Jun. 1992, 89(12):5577-5581.

Petterson et al., "Generations of sequencing technologies," Genomics, 2009, 93(2):105-111.

Picelli et al., "Tn5 transposase and tagmentation procedures for massively scaled sequencing projects," Genome Res., Dec. 2014, 24(12):2033-40.

Pipenburg et al., "DNA detection using recombination proteins," PLoS Biol., Jul. 2006, 4(7):e204, 7 pages.

Plasterk, "The Tc1/mariner transposon family," Curr Top Microbiol Immunol., 1996, 204:125-43.

Plongthongkum et al., "Advances in the profiling of DNA modifications: cytosine methylation and beyond," Nature Reviews Genetics, Aug. 2014, 15(10):647-661.

Polsky-Cynkin et al., "Use of DNA immobilized on plastic and agarose supports to detect DNA by sandwich hybridization," Clin. Chem., 1985, 31(9):1438-1443.

U.S. Appl. No. 61/267,363, filed Dec. 7, 2009, 33 pages.

Raab et al., "Human tRNA genes function as chromatin insulators," EMBO J., Jan. 2012, 31(2):330-50.

Ranki et al., "Sandwich hybridization as a convenient method for the detection of nucleic acids in crude samples," Gene, 1983, 21(1-2):77-85.

Reinartz et al., "Massively parallel signature sequencing (MPSS) as a tool for in-depth quantitative gene expression profiling in all organisms," Brief Funct Genomic Proteomic, Feb. 2002, 1(1):95-104.

Reznikoff, "Tn5 as a model for understanding DNA transposition," Mol Microbiol., Mar. 2003, 47(5):1199-206.

Ristic et al., "Detection of Protein-Protein Interactions and Post-translational Modifications Using the Proximity Ligation Assay: Application to the Study of the SUMO Pathway," Methods Mol. Biol., 2016, 1449:279-90.

Rodriques et al., "Slide-seq: A scalable technology for measuring genome-wide expression at high spatial resolution," Science, 2019, 363(6434):1463-1467.

Ronaghi et al., "A sequencing method based on real-time pyrophosphate," Science, Jul. 1998, 281(5375):363-365.

Ronaghi et al., "Real-time DNA sequencing using detection of pyrophosphate release," Analytical Biochemistry, Nov. 1996, 242(1):84-89.

Ronaghi, "Pyrosequencing sheds light on DNA sequencing," Genome Res, Jan. 2001, 11(1):3-11.

Roy et al., "Assessing long-distance RNA sequence connectivity via RNA-templated DNA-DNA ligation," eLife, 2015, 4:e03700, 21 pages.

(56) References Cited

OTHER PUBLICATIONS

Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schweitzer et al., "Multiplexed protein profding on microarrays by rolling-circle amplification," Nature Biotechnology, Apr. 2002, 20(4):359-365.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Trejo et al., "Extraction-free whole transcriptome gene expression analysis of FFPE sections and histology-directed subareas of tissue," PLoS One, Feb. 2019, 14(2):e0212031, 22 pages.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.

Van Gelder et al., "Amplified RNA synthesized from limited quantities of heterogeneous cDNA," Proc. Natl. Acad. Sci. USA, 1990, 87(5):1663-1667.
Vandemoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019, 116(22):10842-10851.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Weimeich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.

(56) References Cited

OTHER PUBLICATIONS

Zhang et al., "Binding-induced DNA assembly and its application to yoctomole detection of proteins," Anal Chem, 2012, 84(2):877-884.

Zhang et al., "Multiplex ligation-dependent probe amplification (MLPA) for ultrasensitive multiplexed microRNA detection using ribonucleotide-modified DNA probes†," Chem. Commun., 2013, 49:10013-10015.

Zheng et al., "Origins of human mitochondrial point mutations as DNA polymerase gamma-mediated errors," Mutat. Res., 2006, 599(1-2):11-20.

Zhou et al., "Genetically encoded short peptide tags for orthogonal protein labeling by Sfp and AcpS phosphopantetheinyl transferases," ACS Chemical Biol., 2007, 2(5):337-346.

Zhu et al., "Reverse transcriptase template switching: a SMART approach for full-length cDNA library construction," Biotechniques, Apr. 2001, 30(4):892-897.

Al-Ani et al., "Oxygenation in cell culture: Critical parameters for reproducibility are routinely not reported," PLoS One, Oct. 2018, 13(10):e0204269, 13 pages.

Chen et al., "Gray-scale photolithography using microfluidic photomasks," PNAS, Feb. 2003, 100(4):1499-1504.

Dalma-Weiszhausz et al., "The affymetrix GeneChip platform: an overview," Methods Enzymol., 2006, 410:3-28.

Ebihara et al., "Molecular detection of dermatophytes and nondermatophvtes in onychomycosis by nested polymerase chain reaction based on 28S ribosomal RNA gene sequences." Br J Dermatol., Nov. 2009, 161(5):1038-44.

Escholarship.org [online], "Methods and devices for fabricating and assembling DNA and protein arrays for high-throughput analyses [electronic resource]," 2010, retrieved on Jun. 8, 2022, retrieved from URL<https://escholarship.org/uc/item/6tf7p46s>, 155 pages.

Fischer et al., "Hematoxylin and eosin staining of tissue and cell sections," CSH Protoc., May 2008, 3(5):1-3.

Jennane et al., "Photolithography of self-assembled monolayers: optimization of protecting groups by an electroanalytical method," Can. J Chem., Dec. 1996, 74(12):2509-2517.

Lahiani et al., "Enabling Histopathological Annotations on Immunofluorescent Images through Virtualization of Hematoxylin and Eosin," J Pathol Inform., Feb. 2018, 9:1, 8 pages.

Miller et al., "Chapter 11—Solid and Suspension Microarrays for Microbial Diagnostics," Methods in Microbiology, 2015, 42:395-431.

Ren et al., "Star Polymers," Chem Rev., Jun. 2016, 116(12):6743-836.

Totet et al., "Immunocompetent infants as a human reservoir for Pneumocystis jirovecii: rapid screening by non-invasive sampling and real-time PCR at the mitochondrial large subunit rRNA gene," J Eukaryot Microbiol., 2003, pp. 668-669.

Vickovic et al., "SM-Omics: An automated Platform for High-Throughput Spatial Multi-Omics," bioRxiv, Oct. 2020, 40 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.

Anacyte.com [online], "CellCover," 2022, retrieved on Mav 23, 2022, retrieved from URL<https://www.anacyte.com/>, 15 pages.

Asp et al., "Spatially Resolved Transcriptomes-Next Generation Tools for Tissue Exploration," Bioessays, Oct. 2020, 42(10):e1900221, 16 pages.

Balakrishnan et al., "Flap endonuclease 1," Annu Rev Biochem., Jun. 2013, 82:119-138.

Barnett et al., "ATAC-Me Captures Prolonged DNA Methvlation of Dynamic Chromatin Accessibility Loci during Cell Fate Transitions," Mol Cell., Mar. 2020, 77(6):1350-1364.e6.

Bergenstråhle et al., "Seamless integration of image and molecular analysis for spatial transcriptomics workflows," BMC Genomics, Jul. 2020, 21(1):482, 7 pages.

Berger et al., "Universal bases for hybridization, replication and chain termination," Nucleic Acid Res., Aug. 2000, 28(15):2911-2914.

Biolegend.com [online], "Microscopy," 2022, retrieved on May 23, 2022, retrieved from URL<https://www.biolegend.com/en-us/microscopy#applications-fivecolorfluorescencemiscroscopy>, 4 pages.

Blair et al., "Microarray temperature optimization using hybridization kinetics," Methods Mol Biol., 2009, 529:171-96.

Bolotin et al., "MiXCR: software for comprehensive adaptive immunity profiling," Nat Methods., May 2015, 12(5):380-1.

Chen et al., "Parallel single nucleotide polymorphism genotyping by surface invasive cleavage with universal detection," Anal Chem., Apr. 2005, 77(8):2400-5.

Chester et al., "Dimethyl sulfoxide-mediated primer Tm reduction: a method for analyzing the role of renaturation temperature in the polymerase chain reaction," Anal Biochem, Mar. 1993, 209(2):284-90.

Ciaccio et al., "Systems analysis of EGF receptor signaling dynamics with microwestern arrays," Nat Methods, Feb. 2010, 7(2):148-55.

Cruz et al., "Methylation in cell-free DNA for early cancer detection," Ann Oncol., Jun. 2018, 29(6):1351-1353.

Gerard et al., "Excess dNTPs minimize RNA hydrolysis during reverse transcription," Biotechniques, Nov. 2002, 33(5):984, 986, 988, 990.

Hamaguchi et al., "Direct reverse transcription-PCR on oligo(dT)-immobilized polypropylene microplates after capturing total mRNA from crude cell lysates," Clin Chem., Nov. 1998, 44(11):2256-63.

Hessner et al., "Genotyping of factor V G1691A (Leiden) without the use of PCR by invasive cleavage of oligonucleotide probes," Clin Chem., Aug. 2000, 46(8 Pt 1):1051-6.

Hoffman et al., "Formaldehyde crosslinking: a tool for the study of chromatin complexes," J Biol Chem., Oct. 2015, 290(44):26404-11.

Hughes et al., "Microfluidic Western blotting," PNAS, Dec. 2012, 109(52):21450-21455.

Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.

Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.

Jucá et al., "Effect of dimethyl sulfoxide on reverse transcriptase activity," Braz. J. Med. Biol. Res., Mar. 1995, 28(3):285-90.

Kalantari et al., "Deparaffinization of formalin-fixed paraffin-embedded tissue blocks using hot water instead of xylene," Anal Biochem., Aug. 2016, 507:71-3.

Ke et al., "In situ sequencing for RNA analysis in preserved tissue and cells," Nat Methods., Sep. 2013, Supplementary Materials, 29 pages.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining bv chlorella virus DNA ligase and a novel iLock assay with improved direct RNA detection accuracy," Nucleic Acids Research, Oct. 2017, 45(18):e161, 9 pages.

Lou et al., "A review of room temperature storage of biospecimen tissue and nucleic acids for anatomic pathology laboratories and biorepositories," Clin Biochem., Mar. 2014, 47(4-5):267-73.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Lykidis et al., "Novel zinc-based fixative for high quality DNA, RNA and protein analysis," Nucleic Acids Res., Jun. 2007, 35(12):e85, 10 pages.

(56) References Cited

OTHER PUBLICATIONS

Madissoon et al., "scRNA-seq assessment of the human lung, spleen, and esophagus tissue stability after cold preservation," Genome Biol., Dec. 2019, 21(1):1, 16 pages.

Miner et al., "Molecular barcodes detect redundancy and contamination in hairpin-bisulfite PCR," Nucleic Acids Res., Sep. 2004, 32(17):e135, 4 pages.

Nadji et al., "Immunohistochemistiy of tissue prepared by a molecular-friendly fixation and processing system," Appl Immunohistochem Mol Morphol., Sep. 2005, 13(3):277-82.

Niedringhaus et al., "Landscape of next-generation sequencing technologies," Anal Chem., Jun. 2011, 83(12):4327-41.

Nilsson et al., "RNA-templated DNA ligation for transcript analysis," Nucleic Acids Res., Jan. 2001, 29(2):578-81.

Olivier, "The Invader assay for SNP genotyping," Mutat. Res., Jun. 2005, 573(1-2):103-110.

Passow et al., "RNAlater and flash freezing storage methods nonrandomly influence observed gene expression in RNAseq experiments," bioRxiv, Jul. 2018, 28 pages.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perocchi et al., "Antisense artifacts in transcriptome microarray experiments are resolved by actinomycin D," Nucleic Acids Res., 2007, 35(19):e128, 7 pages.

Picelli et al., "Full-length RNA-seq from single cells using Smart-seq2," Nat Protoc., Jan. 2014, 9(1):171-81.

Porreca et al., "Polony DNA sequencing," Curr Protoc Mol Biol., Nov. 2006, Chapter 7, Unit 7.8, pp. 7.8.1-7.8.22.

Qiu et al., "Combination probes with intercalating anchors and proximal fluorophores for DNA and RNA detection," Nucleic Acids Research, Sep. 2016, 44(17):e138, 12 pages.

Schouten et al., "Relative quantification of 40 nucleic acid sequences by multiplex ligation-dependent probe amplification," Nucleic Acids Res., Jun. 2002. 30(12):e57, 13 pages.

Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.

Singh et al., "High-throughput targeted long-read single cell sequencing reveals the clonal and transcriptional landscape of lymphocytes," Nat Commun., Jul. 2019, 10(1)):3120, 13 pages.

Sountoulidis et al., "SCRINSHOT, a spatial method for single-cell resolution mapping of cell states in tissue sections," PLoS Biol., Nov. 2020, 18(11):e3000675, 32 pages.

Spiess et al., "A highly efficient method for long-chain cDNA synthesis using trehalose and betaine," Anal. Biochem., Feb. 2002, 301(2):168-74.

Sutherland et al., "Utility of formaldehyde cross-linking and mass spectrometry in the study of protein-protein interactions," J. Mass Spectrom., Jun. 2008, 43(6):699-715.

Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.

Tu et al., "TCR sequencing paired with massively parallel 3' RNA-seq reveals clonotypic T cell signatures," Nature Immunology, Dec. 2019, 20(12):1692-1699.

Vázquez Bernat et al., "High-Quality Library Preparation for NGS-Based Immunoglobulin Germline Gene Inference and Repertoire Expression Analysis," Front Immunol., Apr. 2019, 10:660, 12 pages.

Wang et al., "Tagmentation-based whole-genome bisulfite sequencing," Nature Protocols, Oct. 2013, 8(10):2022-2032.

Wohnhaas et al., "DMSO cryopreservation is the method of choice to preserve cells for droplet-based single-cell RNA sequencing," Scientific Reports, Jul. 2019, 9(1):10699, 14 pages.

Wu et al., "RollFISH achieves robust quantification of single-molecule RNA biomarkers in paraffin-embedded tumor tissue samples," Commun Biol., Nov. 2018, 1:209, 8 pages.

Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.

Zhao et al., "Isothermal Amplification of Nucleic Acids," Chemical Reviews, Nov. 2015, 115(22):12491-12545.

U.S. Appl. No. 16/353,937, Frisen et al.

U.S. Appl. No. 17/707,189, Chell et al.

Wang et al., "Optimization of Process Conditions for Infected Animal Tissues by Alkaline Hydrolysis Technology," Procedia Environmental Sciences, 2016, 31:366-374.

\* cited by examiner

METHODS FOR DETERMINING A LOCATION OF AN ANALYTE IN A BIOLOGICAL SAMPLE

CROSS-REFERENCE TO RELATED APPLICATIONS

Pursuant to 35 U.S.C. § 119(e), this application is a continuation of International Application PCT/US2021/036557, with an international filing date of Jun. 9, 2021, which claims priority to U.S. Provisional Patent Application No. 63/037,458, filed on Jun. 10, 2020, the entire contents of which are incorporated herein by reference.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Some techniques for studying spatial heterogeneity of a biological sample can cause analytes (e.g., nucleic acid) from the biological sample to diffuse to areas adjacent to the biological sample and be captured in such areas adjacent to the biological sample on the array. The result of capturing analytes on areas adjacent to the biological sample on the array (e.g., areas that do not correlate with the biological sample) can lead to wasted resources, such as unnecessary costs attributed to sequencing (e.g., next generation sequencing). Thus, methods to improve the incidence of captured analytes on areas of the array adjacent to the biological sample, such as blocking probes (e.g., a blocking probe to the capture domain of a capture probe), can improve efficiency, resource conservation, and resolution of the results.

SUMMARY

This application provides for a method to block capture probes on a spatial array that are not directly under the biological sample. The methods described herein can provide an improvement in resource conservation and a reduction and/or elimination of non-specific binding of analytes to unintended portions of the spatial array during performance of any of the methods described herein for determining a location of a target analyte in a biological sample.

Provided herein are methods for determining a location of a target nucleic acid in a biological sample that include: (a) disposing a non-permeabilized biological sample onto an array at a first area, where the array comprises a plurality of capture probes, where: the first area comprises a capture probe of the plurality of capture probes comprising a spatial barcode and a capture domain; and a second area of the array comprises a capture probe of the plurality of capture probes comprising a spatial barcode and a capture domain, and the second area is adjacent to the biological sample disposed on the array; (b) contacting the second area of the array with a solution comprising a blocking probe, where the blocking probe comprises a sequence that binds specifically to the capture domain of the capture probe in the second area of the array; (c) removing residual solution comprising the blocking probe from the second area of the array; (d) permeabilizing the biological sample, such that the capture domain of the capture probe of the first area of the array binds specifically to the target nucleic acid; and (e) determining (i) all or a portion of a sequence corresponding to the spatial barcode of the capture probe of the first area of the array, or a complement thereof, and (ii) all or a portion of a sequence corresponding to the target nucleic acid, or a complement thereof, and using the sequences of (i) and (ii) to determine the location of the target nucleic acid in the biological sample.

In some embodiments of any of the methods described herein, a 3' end of the blocking probe is substantially complementary to about 5 to 100 nucleotides of the capture domain of the capture probe in the second area. In some embodiments of any of the methods described herein, the blocking probe is single-stranded. In some embodiments of any of the methods described herein, the blocking probe is at least partially double-stranded. In some embodiments of any of the methods described herein, a 5' end of the blocking probe is phosphorylated. In some embodiments of any of the methods described herein, step (b) further comprises ligating the 5' end of the blocking probe to a 3' end of the capture probe in the second area. In some embodiments of any of the methods described herein, a 3' end of the blocking probe is chemically blocked. In some embodiments of any of the methods described herein, the 3' end of the blocking probe is chemically blocked by an azidomethyl group. In some embodiments of any of the methods described herein, the blocking probe comprises a hairpin structure. In some embodiments of any of the methods described herein, the blocking probe comprises a locked nucleic acid.

In some embodiments of any of the methods described herein, the method further comprises, between steps (a) and (b), fixing and/or staining the biological sample. In some embodiments of any of the methods described herein, the non-permeabilized biological sample is fixed and/or stained prior to step (a). In some embodiments, the step of fixing the biological sample comprises the use of a fixative selected from the group of ethanol, methanol, acetone, formaldehyde, paraformaldehyde-Triton, glutaraldehyde, and combinations thereof. In some embodiments, the step of staining the biological sample comprises the use of a biological stain selected from the group of: acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, and combinations thereof. In some embodiments, the step of staining the biological sample comprises the use of eosin and hematoxylin. In some embodiments, the step of staining the biological sample comprises the use of a detectable label selected from the group consisting of a radioisotope, a fluorophore, a chemiluminescent compound, a bioluminescent compound, or a combination thereof.

In some embodiments of any of the methods described herein, the biological sample is a tissue sample. In some embodiments, the tissue sample is a tissue section. In some embodiments, the tissue section is a fresh, frozen tissue section. In some embodiments, the biological sample is a clinical sample. In some embodiments, the clinical sample is selected from the group of whole blood, blood-derived products, blood cells, and combinations thereof. In some embodiments, the clinical sample is a cultured tissue. In some embodiments, the clinical sample is cultured cells. In some embodiments, the clinical sample is a cell suspension.

In some embodiments of any of the methods described herein, the biological sample is an organoid, embryonic stem cells, pluripotent stem cells, and combinations thereof. In some embodiments, the organoid is selected from the group of a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, a retinal organoid, and combinations thereof. In some embodiments of any of the methods described herein, the biological sample includes diseased cells, fetal cells, immune cells, cellular macromolecules, organelles, extracellular polynucleotides, and combinations thereof.

In some embodiments of any of the methods described herein, the removing in step (c) comprises washing. In some embodiments of any of the methods described herein, the array comprises a slide. In some embodiments of any of the methods described herein, the array is a bead array. In some embodiments of any of the methods described herein, the determining in step (e) comprises sequencing (i) all or a portion of the sequence corresponding to the spatial barcode of the capture probe of the first area of the array, or a complement thereof, and (ii) all or a portion of the sequence corresponding to the target nucleic acid, or a complement thereof. In some embodiments of any of the methods described herein, the sequencing is high throughput sequencing. In some embodiments of any of the methods described herein, the determining in step (e) comprises extending a 3' end of the capture probe of the first area of the array using the target nucleic acid as a template. In some embodiments of any of the methods described herein, wherein the target analyte is DNA. In some embodiments of any of the methods described herein, the DNA is genomic DNA. In some embodiments of any of the methods described herein, the target analyte is RNA. In some embodiments of any of the methods described herein, the RNA is mRNA. In some embodiments of any of the methods described herein, the method further comprises imaging the biological sample after step (a).

Also provided herein are methods for determining a location of a target analyte in a biological sample, the method comprising: (a) disposing a non-permeabilized biological sample onto an array at a first area, where the array comprises a plurality of capture probes, where: the first area comprises a capture probe of the plurality of capture probes comprising a spatial barcode and a capture domain that binds specifically to the analyte capture sequence; and a second area comprises a capture probe of the plurality of capture probes comprising a spatial barcode and a capture domain, the second area of which is adjacent to the biological sample disposed on the array; (b) contacting a plurality of analyte capture agents with the non-permeabilized biological sample, where an analyte capture agent of the plurality of analyte capture agents comprises an analyte binding moiety barcode, an analyte capture sequence, and an analyte binding moiety that binds specifically to the target analyte; (c) contacting the second area of the array with a solution comprising a blocking probe, where the blocking probe comprises a sequence that binds specifically to the capture domain of the capture probe in the second area of the array; (d) removing residual solution comprising the blocking probe from the second area of the array; (e) permeabilizing the biological sample, such that the capture domain of the capture probe of the first area of the array binds specifically to the analyte capture sequence; and (f) determining (i) all or a portion of the sequence of the spatial barcode of the capture probe in the first area of the array, or a complement thereof, and (ii) all or a portion of the sequence of the analyte binding moiety barcode, or a complement thereof, and using the sequences of (i) and (ii) to determine the location of the target analyte in the biological sample.

In some embodiments of any of the methods described herein, a 3' end of the blocking probe is substantially complementary to about 5 to 100 nucleotides of the capture domain of the capture probe in the second area. In some embodiments of any of the methods described herein, the blocking probe is single-stranded. In some embodiments of any of the methods described herein, the blocking probe is partially double-stranded. In some embodiments of any of the methods described herein, a 5' end of the blocking probe is phosphorylated. In some embodiments of any of the methods described herein, step (c) further comprises ligating the 5' end of the blocking probe to a 3' end of the capture probe in the second area. In some embodiments of any of the methods described herein, a 3' end of the blocking probe is chemically blocked. In some embodiments of any of the methods described herein, the chemical block is an azidomethyl group. In some embodiments of any of the methods described herein, the blocking probe comprises a hairpin structure. In some embodiments of any of the methods described herein, the blocking probe comprises a locked nucleic acid.

In some embodiments of any of the methods described herein, the method further comprises, between steps (b) and (c), fixing the biological sample. In some embodiments of any of the methods described herein, the non-permeabilized biological sample is fixed and/or stained prior to step (a). In some embodiments, the step of fixing the biological sample comprises the use of a fixative selected from the group of ethanol, methanol, acetone, formaldehyde, paraformaldehyde-Triton, glutaraldehyde, and combinations thereof. In some embodiments of any of the methods described herein, staining the biological sample comprises the use of a biological stain selected from the group of: acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, and combinations thereof. In some embodiments, the step of staining the biological sample comprises the use of eosin and hematoxylin. In some embodiments, the step of staining the biological sample comprises the use of a detectable label selected from the group of a radioisotope, a fluorophore, a chemiluminescent compound, a bioluminescent compound, or a combination thereof. In some embodiments of any of the methods described herein, the biological sample is a tissue sample. In some embodiments, the tissue sample is a tissue section. In some embodiments, the tissue section is a fresh, frozen tissue section. In some embodiments of any of the methods described herein, the biological sample is a clinical sample. In some embodiments, the clinical sample is selected from the group of whole blood, blood-derived products, blood cells, and combinations thereof. In some embodiments, the clinical sample is a cultured tissue. In some embodiments, the clinical sample is cultured cells. In some embodiments, the clinical sample is a cell suspension. In some embodiments of any of the methods described herein, the biological sample is an organoid, embryonic stem cells, pluripotent stem cells, and combinations thereof. In some embodiments, the organoid is selected from the group of a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, a retinal organoid, and combinations thereof. In some embodiments of any of the methods described herein, the biological sample includes diseased cells, fetal cells, immune cells, cellular macromolecules, organelles, extracellular polynucleotides, and combinations thereof. In some embodiments of any of the methods described herein, the removing in step (d) comprises washing. In some embodiments of any of the methods described herein, the array comprises a slide. In some embodiments of any of the methods described herein, the array is a bead array.

In some embodiments of any of the methods described herein, the determining in step (f) comprises sequencing (i) all or a portion of the sequence corresponding to the spatial barcode of the capture probe in the first area of the array, or a complement thereof, and (ii) all or a portion of the sequence corresponding to the analyte binding moiety barcode, or a complement thereof. In some embodiments of any of the methods described herein, the sequencing is high throughput sequencing. In some embodiments of any of the methods described herein, the determining in step (f) comprises extending a 3' end of the capture probe of the first area of the array using the analyte binding moiety barcode as a template. In some embodiments of any of the methods described herein, the target analyte is a protein. In some embodiments of any of the methods described herein, the protein is an intracellular protein. In some embodiments of any of the methods described herein, the protein is an extracellular protein. In some embodiments of any of the methods described herein, the analyte binding moiety is an antibody or an antigen-binding moiety thereof. In some embodiments of any of the methods described herein, steps (a) and (b) are performed at substantially the same time. In some embodiments of any of the methods described herein, step (a) is performed before step (b). In some embodiments of any of the methods described herein, step (b) is performed before step (a). In some embodiments of any of the methods described herein, the method further comprises imaging the biological sample after step (b).

Also provided herein are kits comprising an array comprises a plurality of capture probes, where a capture probe of the plurality of capture probes comprising a spatial barcode and a capture domain; and a solution comprising a blocking probe, where the blocking probe comprises a sequence that binds specifically to the capture domain of the capture probe.

In some embodiments of any of the kits described herein, the kit(s) further comprise one or more fixative(s). In some embodiments of any of the kits described herein, the kit(s) further comprise one or more biological stains. In some embodiments, the one or more biological stains is eosin and hematoxylin. In some embodiments of any of the kits described herein, the kit(s) further comprise one or more permeabilization reagent(s). In some embodiments of any of the kits described herein, the one or more permeabilization reagent(s) is selected from the group of an organic solvent, a cross-linking agent, a detergent, an enzyme, and combinations thereof. In some embodiments of any of the kits described herein, the kit further comprises a reverse transcriptase. In some embodiments of any of the kits described herein, the kit further comprises a terminal deoxynucleotidyl transferase. In some embodiments of any of the kits described herein, the kit further comprises a template switching oligonucleotide. In some embodiments of any of the kits described herein, the kit further comprises a DNA polymerase. In some embodiments of any of the kits described herein, the kit further comprises a second strand primer. In some embodiments of any of the kits described herein, the kit further comprises a fragmentation buffer and a fragmentation enzyme. In some embodiments of any of the kits described herein, the kit further comprises a DNA ligase. In some embodiments, the DNA ligase is a T4 DNA ligase. In some embodiments of any of the kits described herein, the kit further comprises one or more adaptor(s). In some embodiments, the one or more adaptor(s) is/are selected from the group of an i5 sample index sequence, an i7 sample index sequence, a P5 sample index sequence, a P7 sample index sequence, and combinations thereof.

Also provided herein are composition(s), comprising an array, where the array comprises a plurality of capture probes, where: the first area comprises a capture probe of the plurality of capture probes comprising a spatial barcode and a capture domain specifically bound to a target analyte from the biological sample; and a second area of the array comprises a capture probe of the plurality of capture probes comprising a spatial barcode and a capture domain specifically bound to a blocking probe, and the second area is adjacent to the biological sample disposed on the array.

In some embodiments of any of the composition(s) described herein, a 3' end of the blocking probe is substantially complementary to about 5 to 100 nucleotides of the capture domain of the capture probe in the second area. In some embodiments of any of the composition(s) described herein, the blocking probe is single-stranded. In some embodiments of any of the composition(s) described herein, the blocking probe is partially double-stranded. In some embodiments of any of the composition(s) described herein, a 5' end of the blocking probe is phosphorylated. In some embodiments of any of the composition(s) described herein, the blocking probe is ligated to a 3' end of the capture probe in the second area. In some embodiments of any of the composition(s) described herein, a 3' end of the blocking probe is chemically blocked. In some embodiments of any of the composition(s) described herein, the chemical block is an azidomethyl group. In some embodiments of any of the composition(s) described herein, the blocking probe comprises a hairpin structure. In some embodiments of any of the composition(s) described herein, the blocking probe comprises a locked nucleic acid.

In some embodiments, a biological sample is disposed on the first area of the array. In some embodiments of any of the composition(s) described herein, the biological sample is a tissue sample. In some embodiments of any of the composition(s) described herein, the tissue sample is a tissue section. In some embodiments of any of the composition(s) described herein, the biological sample is a clinical sample. In some embodiments of any of the composition(s) described herein, the clinical sample is selected from the group of whole blood, blood-derived products, blood cells, and combinations thereof. In some embodiments of any of the composition(s) described herein, the clinical sample is a cultured tissue. In some embodiments of any of the composition(s) described herein, the clinical sample is cultured cells. In some embodiments of any of the composition(s) described herein, the clinical sample is a cell suspension. In some embodiments of any of the composition(s) described herein, the biological sample is an organoid, embryonic stem cells, pluripotent stem cells, and combinations thereof. In some embodiments of any of the composition(s) described herein, the organoid is selected from the group of a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, a retinal organoid, and combinations thereof. In some embodiments of any of the composition(s) described herein, the biological sample includes diseased cells, fetal cells, immune cells, cellular macromolecules, organelles, extracellular polynucleotides, and combinations thereof.

In some embodiments of any of the composition(s) described herein, the array comprises a slide. In some embodiments of any of the composition(s) described herein, the array is a bead array. In some embodiments of any of the composition(s) described herein, the target analyte is DNA. In some embodiments of any of the composition(s) described herein, the DNA is genomic DNA. In some embodiments of any of the composition(s) described herein, the target analyte is RNA. In some embodiments of any of the composition(s) described herein, the RNA is mRNA.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
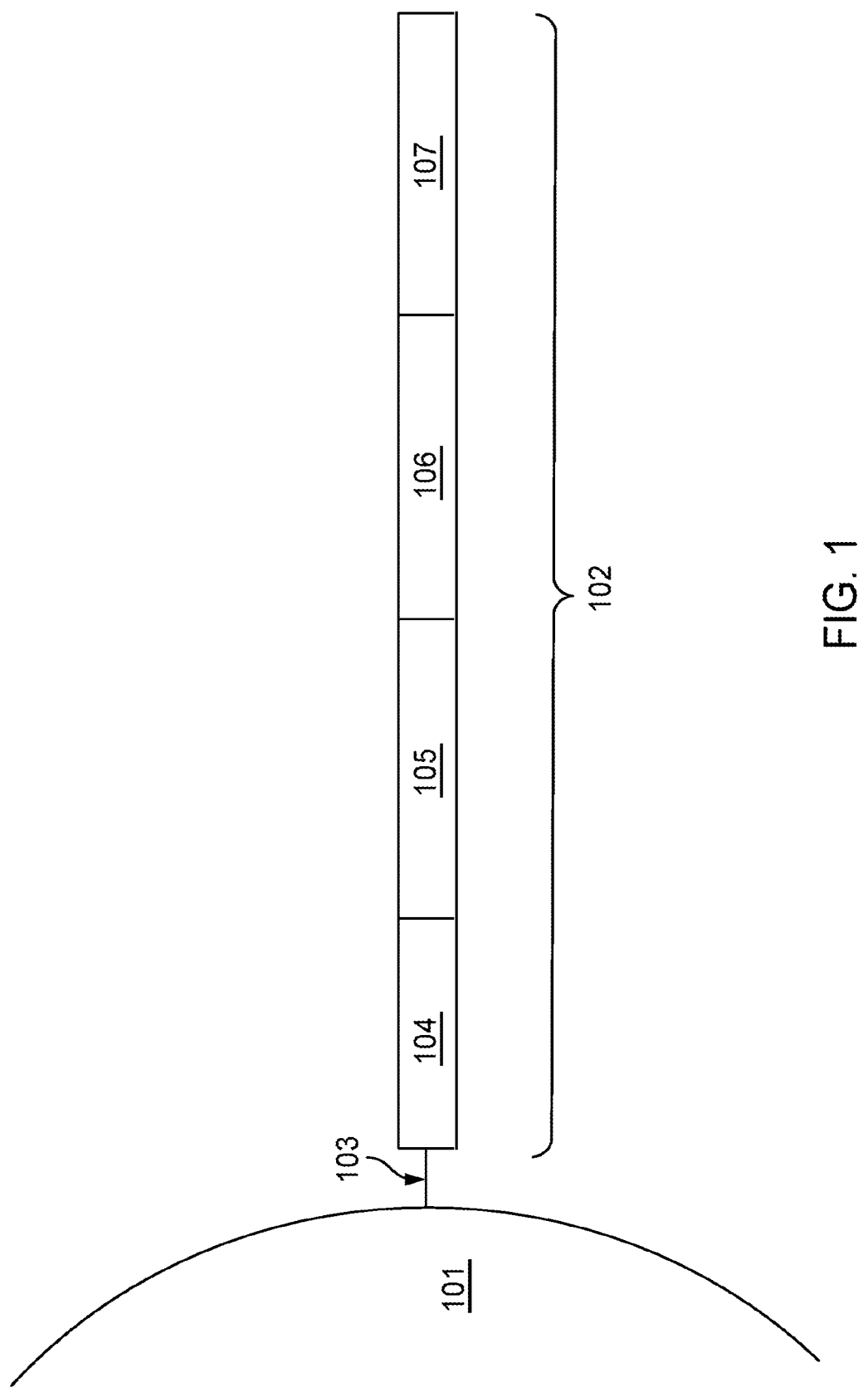
FIG. 1 is a schematic diagram showing an example of a barcoded capture probe, as described herein.

Blocking one or more capture domains of capture probes on spatial arrays (or portions thereof) can increase efficiency and/or decrease non-specific binding of analytes on arrays (or portions thereof). In some cases, one or more capture probes (e.g., capture domain of capture probes) can be blocked with one or more blocking probes. A 3' end of a blocking probe can be substantially complementary to about 5 to about 100 nucleotides of the capture domain. Provided herein are methods, compositions, and kits, e.g., for carrying out these methods. In some cases, a portion of an array can be selectively blocked and/or selectively unblocked.

Methods for reducing non-specific spatial interactions on a spatial array are described herein. Methods herein can improve the resolution of spatial array results by reducing non-specific binding of targeted analytes. For example, methods herein can reduce non-specific binding of target analytes by capture probes (e.g., by blocking the capture domain of capture probes) not proximal to the targeted analyte. In some cases, analytes from a biological sample can diffuse to areas of the array that are adjacent to the biological sample. This can cause analytes to bind to the capture domain(s) of one or more capture probes adjacent to the biological sample. Non-specific binding increases background results (e.g., non-specific results), thereby decreasing resolution. Blocking the capture domain of capture probes that adjacent to the biological sample can decrease the non-specific binding and increase the resolution of results.

Methods described herein can also conserve resources. For example, in some cases, the analysis of spatial arrays can include sequencing. Non-specific binding of analytes to the capture domain of one or more capture probes can result in sequencing of undesired targets. Non-specific analyte capture can cause downstream sequencing inefficiencies, for example, a decrease in the amount of target analyte sequencing due to sequencing of non-specific captured analytes is inefficient and reagent costly and can result in a decrease is spatial resolution. The present disclosure provides solutions for improving and/or preventing non-specific analyte capture on an array slide.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Methods for Reducing Non-Specific Spatial Interactions on a Spatial Array

Spatial tissue arrays allow a researcher to identify gene expression, protein locations, and other cellular activity tracking in a spatial manner. The benefits of correlating spatial biological relationships with diseases and disorders does, and will, continue to advance many fields of scientific study. However, improvements in the resolution of spatial relationships between the cellular activates and diseases and disorders would enhance those data. For example, when a biological sample (e.g., a tissue section) affixed to a spatial array slide is permeabilized to release analytes of interest some of the analytes from the tissue can, via diffusion, move to areas of the array where there is no biological sample (e.g., tissue section), for example adjacent to a biological sample, where non-specific spatial analyte capture can occur. This type of non-specific spatial analyte capture can decrease the resolution of the desired spatial analyte data. Further, non-specific analyte capture can cause downstream sequencing inefficiencies; a decrease in the amount of target analyte sequencing due to sequencing of non-specific captured analytes is inefficient and reagent costly. The present disclosure provides solutions for improving and/or preventing non-specific analyte capture on an array slide.

Provided herein are methods for reducing non-specific analyte capture in a non-permeabilized biological sample (e.g., any of the exemplary biological samples described herein) that include: (a) disposing a non-permeabilized biological sample onto an array (e.g., any of the arrays described herein) at a first area (e.g., any of the first areas described herein), where the array comprises a plurality of capture probes (e.g., any of the exemplary capture probes described herein), where: the first area comprises a capture probe of the plurality of capture probes comprising a spatial barcode (e.g., any of the exemplary spatial barcodes described herein) and a capture domain (e.g., any of the exemplary capture domains described herein); and a second area (e.g., any of the second areas described herein) of the array comprises a capture probe of the plurality of capture probes (e.g., any of the capture probes described herein) comprising a spatial barcode (e.g., any of the spatial barcodes described herein) and a capture domain (e.g., any of the capture domains described herein), and the second area is adjacent to the biological sample disposed on the array; (b) contacting the array with a solution comprising at least one blocking probe (e.g., any of the exemplary blocking probes described herein), where the at least one blocking probe comprises a sequence that binds specifically to the capture domain of the capture probe in the second area of the array; (c) removing residual solution from the array (e.g., washing the array using any of the methods for removing solutions and/or blocking probes described herein); (d) permeabilizing the biological sample (e.g., using any of the methods for permeabilizing a biological sample described herein), such that the capture domain of the capture probe of the first area of the array binds specifically to the target nucleic acid and the target nucleic acid capture in the second area is reduced.

The biological sample can be any of the biological samples described herein. For example, in some embodiments, the biological sample is a tissue sample (e.g., a tissue section). In other embodiments, the biological sample is a clinical sample (e.g., whole blood, blood-derived products, blood cells, cultured tissue, cultured cells, or a cell suspension). In some embodiments, the biological sample is an organoid, embryonic stem cells, pluripotent stem cells, or any combination thereof. Non-limiting examples of an organoid include a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, a retinal organoid, or any combination thereof. In other example embodiments, the biological sample can include diseased cells, fetal cells, immune cells, cellular macromolecules, organelles, extracellular polynucleotides, or any combination thereof.

Non-limiting examples of a target nucleic acid include DNA analytes such as genomic DNA, methylated DNA, specific methylated DNA sequences, fragmented DNA, mitochondrial DNA, in situ synthesized PCR products, and viral DNA.

Non-limiting examples of a target nucleic acid also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA). The RNA can be from an RNA virus, for example RNA viruses from Group III, IV or V of the Baltimore classification system. The RNA can be from a retrovirus, such as a virus from Group VI of the Baltimore classification system.

In some embodiments, the target nucleic acid can include at least 1, at least 2, at least 3, at least 4, at least 5, at least 6, at least 7, at least 8, at least 9, or at least 10 disease-causing mutations (e.g., cancer-causing mutations). In some embodiments, the target nucleic acid includes a single nucleotide polymorphism, gene amplification, or chromosomal translocation, deletion or insertion.

In some embodiments, the biological sample can be fixed (e.g., between steps (a) and (b) the biological sample can be fixed using any of the techniques described herein or known in the art). In some embodiments, fixing the biological sample comprises the use of a fixative selected from the group of ethanol, methanol, acetone, formaldehyde, formalin, paraformaldehyde-Triton, glutaraldehyde, or any combination thereof. In some embodiments, a fixed biological sample is a formalin fixed paraffin embedded tissue sample.

In some embodiments, the biological sample can be stained and/or imaged using any of the techniques described herein or known in the art (e.g., the biological sample can be stained and/or imaged between steps (a) and (b)). In some embodiments, the staining includes optical labels as described herein, including, but not limited to, fluorescent (e.g., fluorophore), radioactive (e.g., radioisotope), chemiluminescent (e.g., a chemiluminescent compound), a bioluminescent compound, calorimetric, or colorimetric detectable labels. In some embodiments, the staining includes a fluorescent antibody directed to a target analyte (e.g., cell surface or intracellular proteins) in the biological sample. In some embodiments, the staining includes an immunohistochemistry stain directed to a target analyte (e.g., cell surface or intracellular proteins) in the biological sample. In some embodiments, the staining includes a chemical stain, such as hematoxylin and eosin (H&E) or periodic acid-schiff (PAS). In some embodiments, staining the biological sample comprises the use of a biological stain including, but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof. In some embodiments, significant time (e.g., days, months, or years) can elapse between staining and/or imaging the biological sample.

Methods for Determining a Location of a Target Analyte

Also provided herein are methods for determining a location of a target analyte in a non-permeabilized biological sample that include: (a) disposing a non-permeabilized biological sample onto an array (e.g., any of the example arrays described herein) at a first area (e.g., any of the first areas described herein), where the array comprises a plurality of capture probes (e.g., any of the exemplary capture probes described herein), where: the first area comprises a capture probe (e.g., any of the capture probes described herein) of the plurality of capture probes comprising a spatial barcode (e.g., any of the spatial barcodes described herein) and a capture domain (e.g., any of the capture domains described herein) that binds specifically to the analyte capture sequence; and a second area (e.g., any of the second areas described herein) comprises a capture probe (e.g., any of the capture probes described herein) of the plurality of capture probes comprising a spatial barcode (e.g., any of the spatial barcodes described herein) and a capture domain (e.g., any of the capture domains described herein), the second area of which is adjacent to the biological sample disposed on the array; (b) contacting a plurality of analyte capture agents (e.g., any of the analyte capture agents described herein) with the non-permeabilized biological sample (e.g., any of the biological samples described herein), where an analyte capture agent of the plurality of analyte capture agents comprises an analyte binding moiety barcode (e.g., any of the analyte binding moiety barcodes described herein), an analyte capture sequence (e.g., any of the analyte capture sequences described herein), and an analyte binding moiety (e.g., any of the analyte binding moieties described herein) that binds specifically to the target analyte; (c) contacting the array with a solution comprising a blocking probe (e.g., any of the blocking probes described herein), where the blocking probe comprises a sequence that binds specifically to the capture domain of the capture probe in the second area of the array; (d) removing residual solution (e.g., washing the array using any of the methods for removing solutions and/or blocking probes described herein) comprising the blocking probe from the second area of the array; (e) permeabilizing the biological sample (e.g., using any of the methods for permeabilizing the biological sample described herein), such that the capture domain of the capture probe of the first area of the array binds specifically to the analyte capture sequence; and (f) determining (i) all or a portion of a sequence corresponding to the spatial barcode of the capture probe in the first area of the array, or a complement thereof, and (ii) all or a portion of a sequence corresponding to the analyte binding moiety barcode, or a complement thereof, and using the sequences of (i) and (ii) to determine the location of the target analyte in the biological sample.

First and Second Areas

In some embodiments of any of the methods described herein, an array can have a first area upon which is disposed a biological sample and a second area that is adjacent to the biological sample. For instance, some embodiments of any of the methods described herein include disposing a biological sample (e.g., a non-permeabilized biological sample) onto an array (e.g., any of the exemplary arrays described herein), where the array then has a first area covered by the non-permeabilized biological sample and a second area not covered by the non-permeabilized biological sample.

In some examples, the first area can represent a portion of the array that is covered by the biological sample, e.g., about 10% to about 99%, about 10% to about 95%, about 10% to about 90%, about 10% to about 85%, about 10% to about 80%, about 10% to about 75%, about 10% to about 70%, about a 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 99%, about 15% to about 95%, about 15% to about 90%, about 15% to about 85%, about 15% to about 80%, about 15% to about 75%, about 15% to about 70%, about a 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 15% to about 20%, about 20% to about 99%, about 20% to about 95%, about 20% to about 90%, about 20% to about 85%, about 20% to about 80%, about 20% to about 75%, about 20% to about 70%, about a 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 99%, about 25% to about 95%, about 25% to about 90%, about 25% to about 85%, about 25% to about 80%, about 25% to about 75%, about 25% to about 70%, about a 25% to about 65%, about 25% to about 60%, about 25% to about 55%, about 25% to about 50%, about 25% to about 45%, about 25% to about 40%, about 25% to about 35%, about 25% to about 30%, about 30% to about 99%, about 30% to about 95%, about 30% to about 90%, about 30% to about 85%, about 30% to about 80%, about 30% to about 75%, about 30% to about 70%, about a 30% to about 65%, about 30% to about 60%, about 30% to about 55%, about 30% to about 50%, about 30% to about 45%, about 30% to about 40%, about 30% to about 35%, about 35% to about 99%, about 35% to about 95%, about 35% to about 90%, about 35% to about 85%, about 35% to about 80%, about 35% to about 75%, about 35% to about 70%, about a 35% to about 65%, about 35% to about 60%, about 35% to about 55%, about 35% to about 50%, about 35% to about 45%, about 35% to about 40%, about 40% to about 99%, about 40% to about 95%, about 40% to about 90%, about 40% to about 85%, about 40% to about 80%, about 40% to about 75%, about 40% to about 70%, about a 40% to about 65%, about 40% to about 60%, about 40% to about 55%, about 40% to about 50%, about 40% to about 45%, about 45% to about 99%, about 45% to about 95%, about 45% to about 90%, about 45% to about 85%, about 45% to about 80%, about 45% to about 75%, about 45% to about 70%, about a 45% to about 65%, about 45% to about 60%, about 45% to about 55%, about 45% to about 50%, about 50% to about 99%, about 50% to about 95%, about 50% to about 90%, about 50% to about 85%, about 50% to about 80%, about 50% to about 75%, about 50% to about 70%, about a 50% to about 65%, about 50% to about 60%, about 50% to about 55%, about 55% to about 99%, about 55% to about 95%, about 55% to about 90%, about 55% to about 85%, about 55% to about 80%, about 55% to about 75%, about 55% to about 70%, about a 55% to about 65%, about 55% to about 60%, about 60% to about 99%, about 60% to about 95%, about 60% to about 90%, about 60% to about 85%, about 60% to about 80%, about 60% to about 75%, about 60% to about 70%, about a 60% to about 65%, about 65% to about 99%, about 65% to about 95%, about 65% to about 90%, about 65% to about 85%, about 65% to about 80%, about 65% to about 75%, about 65% to about 70%, about 70% to about 99%, about 70% to about 95%, about 70% to about 90%, about 70% to about 85%, about 70% to about 80%, about 70% to about 75%, about 75% to about 99%, about 75% to about 95%, about 75% to about 90%, about 75% to about 85%, about 75% to about 80%, about 80% to about 99%, about 80% to about 95%, about 80% to about 90%, about 80% to about 85%, about 85% to about 99%, about 85% to about 95%, about 85% to about 90%, about 90% to about 99%, about 90% to about 95%, or about 95% to about 99%, of the total area of the array covered by the biological sample.

The second area represents a portion of the array that is not covered by the biological sample.

Figure 2:
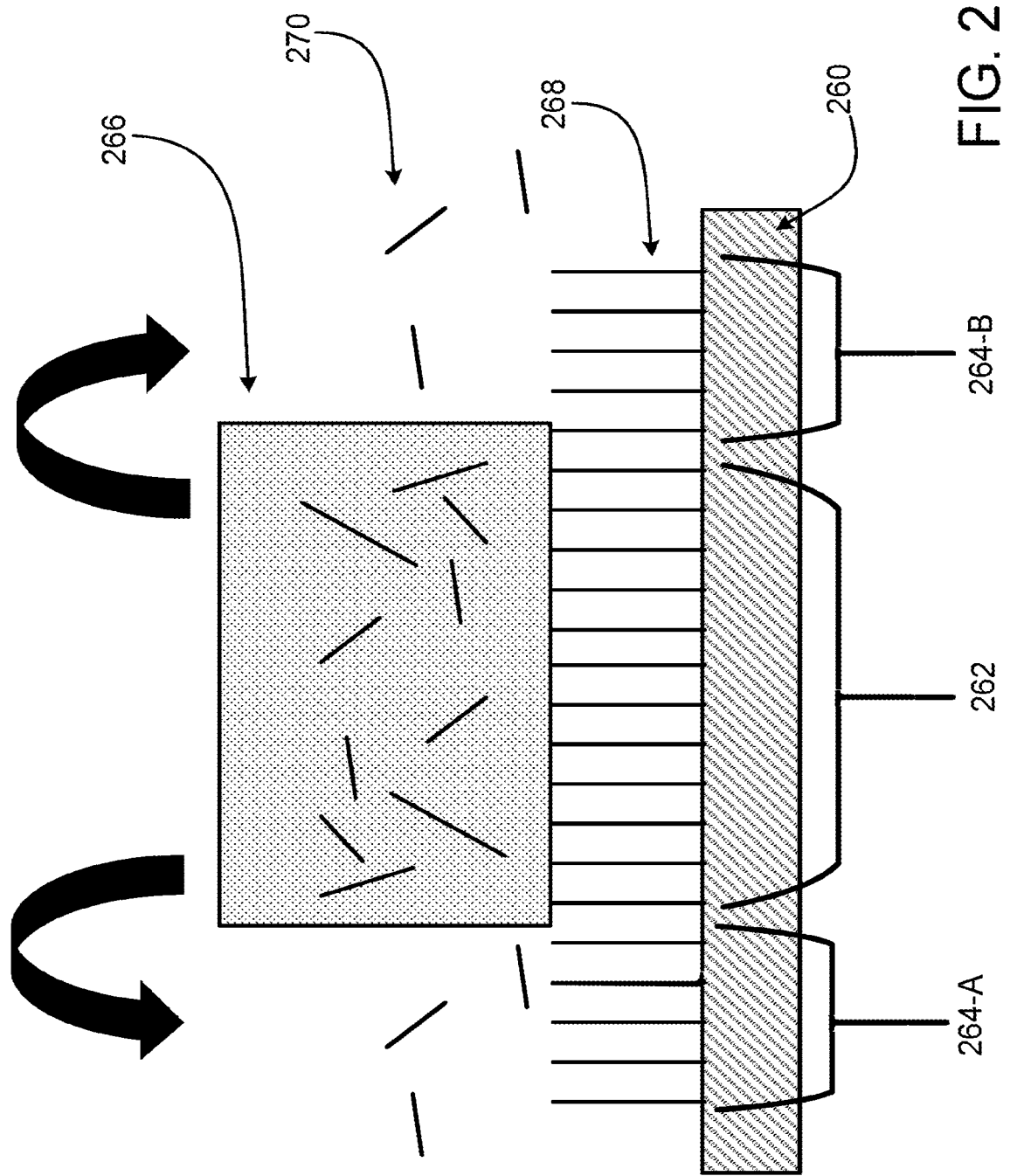
FIG. 2 shows an example of diffusion of target nucleic acids away from a biological sample towards an unintended area of an array.

FIG. 2 shows an example of diffusion of target nucleic acids away from the first area of the array towards the second area of the array, the areas adjacent to a biological sample on an array. FIG. 2 shows a substrate 260 including a first area 262 covered by a non-permeabilized biological sample 266 and one or more second areas 264-A and 264-B, where there is no biological sample (e.g., the areas adjacent to the biological sample). The capture probes 268 are inferior to the biological sample 266 and adjacent thereto (264-A and 264-B). The biological sample 266 includes an analyte, for example one or more target nucleic acids 270. While two second areas 264-A and 264-B are shown in FIG. 2, the second areas described herein are not so limited. For example, a second area of an array is any area that is not covered by a biological sample, so areas around the biological sample and areas distal to the biological sample in all directions are considered second areas. Likewise, although FIG. 2 shows a single first area 262, the first areas described herein are not so limited. For example, a first area is any area that has a biological sample on it, so an area wherein the capture probes on the array are covered by a biological sample (e.g., the biological sample is superior to the capture probes). The first or second areas described herein can have a regular or irregular shape.

The first and second areas can comprise a capture probe of the plurality of capture probes 268 comprising a spatial barcode and a capture domain. During permeabilization and/or selective permeabilization using any of the methods discussed herein (e.g., acetone, electrophoresis, selective permeabilization, etc.), the target nucleic acids 270 can, in some examples, (indicated by the arrows of FIG. 2) diffuse into the second area(s) 264-A and 264-B. The capture of the target nucleic acids 270 on one or more second areas 264-A and 264-B result in non-specific spatial target analyte capture which can result in a waste of resources e.g., sequencing reads of the non-specific regions of the second area(s) 264-A and 264-B and possible decrease in spatial resolution. In some embodiments, contacting one or more of the second area(s) 264-A and 264-B with a solution including one or more blocking probes, where the blocking probe comprises a sequence that binds to the capture domain of the capture probe in the second area 264-A and 264-B, before the biological sample 266 is permeabilized, can prevent the capture of the target nucleic acids 270 to the second areas 264-A and 264-B. In some embodiments, a solution including one or more blocking probes can be applied to the first area 262 and one or more of the second area(s) 264-A and 264-B.

Blocking Probes

Non-limiting examples of blocking probes can include standard DNA probes that are modified to not prime amplification, peptide nucleic acid (PNA) probes, modified RNA nucleotides such as locked nucleic acids (LNAs), among others. In some embodiments, the blocking probe is used to block or modify the free 3' end of the capture domain of the capture probes in the second area of the array. In some embodiments, the blocking probe can include a hairpin structure. In some examples, the blocking probe can include a hairpin structure. In some embodiments, blocking probes can be hybridized to the capture domain of the capture probes in the second area of the array thereby blocking or masking the free 3' end of the capture domain, e.g., PNAs, LNAs, standard DNA probes, hairpin probes, partially double-stranded probes, or complementary sequences. In some embodiments, a free 3' end of a capture domain of the capture probes included in the second area can be blocked by chemical modification, e.g., addition of an azidomethyl group as a chemically reversible capping moiety such that the capture probes do not include a free 3' end. Blocking or modifying the capture probes in the second area of the array, particularly the free 3' end of a capture domain of the capture probes prevents the capture of a target analyte, such as a poly(A) tail of a mRNA, to the free 3' end of the capture probes thereby decreasing or eliminating non-specific analyte capture in those areas.

Figure 3A:
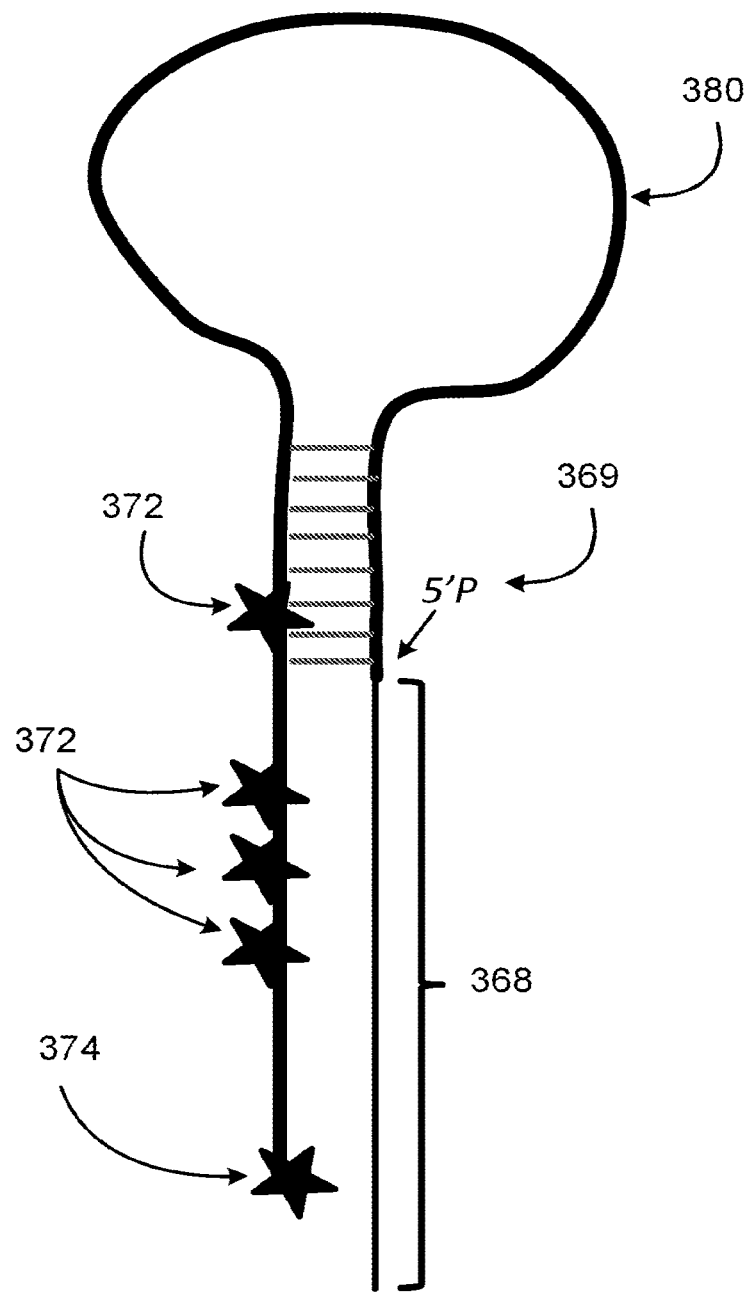
FIG. 3A shows an exemplary blocking probe comprising a hairpin structure bound to a capture domain of a capture probe.
Figure 3B:
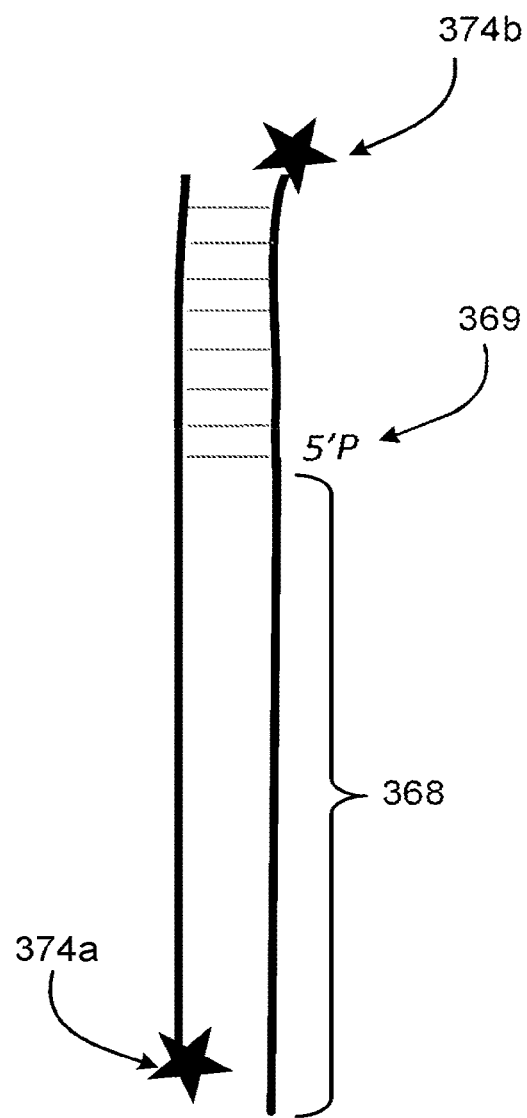
FIG. 3B shows an exemplary partially-double stranded blocking probe bound to a capture domain of a capture probe.

FIG. 3A shows an exemplary blocking probe 380 bound to a capture domain of a capture probe and FIG. 3B shows an exemplary blocking probe bound to a capture domain of a capture probe. The exemplary blocking probe 380 shown in FIG. 3A comprises a hairpin structure and a phosphorylated 5' end 369 that can be ligated to the capture domain of the capture probe 368 in the second area of an array. The blocking probe 380 shown in FIG. 3A can optionally include modifications 372 to enhance hybridization. A non-limiting example of an optional modification to enhance hybridization includes the utilization of locked nucleic acids. The 3' end 374 of the exemplary blocking probe 380 shown in FIG. 3A can be chemically blocked to prevent extension by polymerases. A non-limiting example of chemical blocking group is an azidomethyl group, which when added to a 3' end of the blocking probe prevents extension of the 3' end of the blocking probe.

FIG. 3B shows another example of a blocking probe including a partially double-stranded structure. The example blocking probe shown in FIG. 3B can have a phosphorylated 5' end 369 that can be ligated to the 3' end of the capture domain of the capture probe 368 in the second area of an array. A 3' end 374a and/or 374b of the exemplary blocking probe shown in FIG. 3B can be chemically blocked to prevent extension by polymerases. A non-limiting example of a chemical blocking group is an azidomethyl group.

In some embodiments, the blocking probe can be substantially complementary to about 5 to about 150 nucleotides (e.g., about 5 nucleotides to about 140 nucleotides, about 5 nucleotides to about 120 nucleotides, about 5 nucleotides to about 100 nucleotides, about 5 nucleotides to about 80 nucleotides, about 5 nucleotides to about 60 nucleotides, about 5 nucleotides to about 40 nucleotides, about 5 nucleotides to about 20 nucleotides, about 5 nucleotides to about 15 nucleotides, about 10 nucleotides to about 150 nucleotides, about 10 nucleotides to about 120 nucleotides, about 10 nucleotides to about 100 nucleotides, about 10 nucleotides to about 80 nucleotides, about 10 nucleotides to about 60 nucleotides, about 10 nucleotides to about 40 nucleotides, about 10 nucleotides to about 20 nucleotides, about 20 nucleotides to about 150 nucleotides, about 20 nucleotides to about 120 nucleotides, about 20 nucleotides to about 100 nucleotides, about 20 nucleotides to about 80 nucleotides, about 20 nucleotides to about 60 nucleotides, about 20 nucleotides to about 40 nucleotides, about 20 nucleotides to about 30 nucleotides, about 40 nucleotides to about 150 nucleotides, about 40 nucleotides to about 120 nucleotides, about 40 nucleotides to about 100 nucleotides, about 40 nucleotides to about 80 nucleotides, about 40 nucleotides to about 60 nucleotides, about 60 nucleotides to about 150 nucleotides, about 60 nucleotides to about 120 nucleotides, about 60 nucleotides to about 100 nucleotides, about 60 nucleotides to about 80 nucleotides, about 80 nucleotides to about 150 nucleotides, about 80 nucleotides to about 120 nucleotides, about 80 nucleotides to about 100 nucleotides, about 100 nucleotides to about 150 nucleotides, or about 100 nucleotides to about 130 nucleotides), of the capture domain of the capture probe in the second area and/or the capture domain of the capture probe in the first area.

Figure 4:
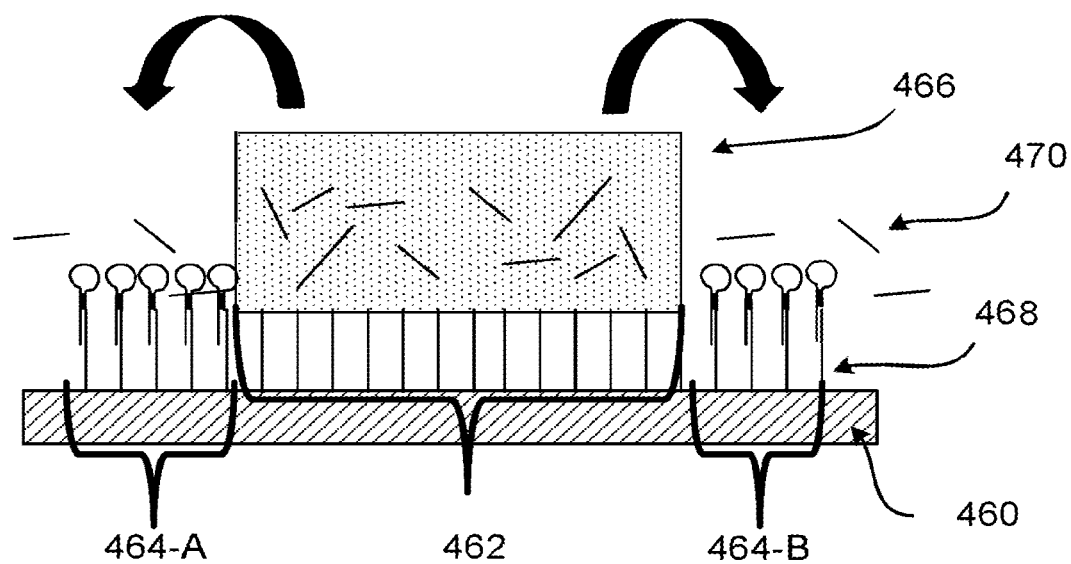
FIG. 4 shows an exemplary embodiment of blocked capture probes in the area of a spatial array that is not under a biological sample, where the block is the hairpin structure of FIG. 3A.

FIG. 4 shows an exemplary embodiment of blocked capture probes in the area of a spatial array that is not under a biological sample, where the block is the hairpin structure of FIG. 3A. FIG. 4 shows a substrate 460 of an array including a first area 462 covered by a non-permeabilized biological sample 466 and second areas 464-A and 464-B. The array comprises a plurality of capture probes 468. The biological sample 466 includes a target nucleic acid 470. While two second areas 464-A and 464-B are shown in FIG. 4, the methods described herein are not so limited. The first area 462 can include a capture probe of the plurality of capture probes 468 comprising a spatial barcode and a capture domain. The one or more second areas 464-A and 464-B can comprise a capture probe of the plurality of capture probes 468 comprising a spatial barcode and a capture domain. During permeabilization and/or selective permeabilization using any methods discussed herein (e.g., acetone, electrophoresis, selective lysing, etc.) the target nucleic acid 470 can, in some examples, diffuse (indicated by the arrows of FIG. 4) to the second area(s) 464-A and 464-B of the array. The binding of the target nucleic acid 470 to capture domains of capture probes in one or more second areas 464-A and 464-B can cause non-specific analyte capture which can result in a waste of resources. To avoid the non-specific analyte capture of the target nucleic acid 470 to the second area(s) 464-A and 464-B of the array, blocking probes as described in FIG. 3A can be contacted to the second area (optionally in combination with a ligase). Contacting the second area(s) 464-A and 464-B of the array, and not the first area 462 of the array (because it is protected by the biological sample 466), with a solution including a blocking probe, where the blocking probe comprises a sequence that binds specifically to the capture domain of the capture probe in the second area(s) 464-A and 464-B of the array prevent(s) analyte capture of the target nucleic acid to the second area(s) 464-A and 464-B of the array. A blocking probe of FIG. 3B could also be used in FIG. 4, however this is not shown.

Contacting the Second Area of the Array with a Solution Comprising a Blocking Probe.

In some embodiments, the solution comprising one or more blocking probes is added automatically (e.g., by a device e.g., a robot) or manually (e.g., by pipetting) to the second area of the array. In some embodiments, the solution comprising a blocking probe is added dropwise by a pipette. In some embodiments, the solution comprising a blocking probe is added to contact all or a portion of the second area of the array. In some embodiments, the solution comprising a blocking probe is added to all or a portion of a surface of the non-permeabilized biological sample that is not facing or contacting the array. In some embodiments, the solution comprising the blocking probe is added to the whole array.

In some embodiments, the solution is added vertically above the second area of the array. In some embodiments, the solution is present in liquid form, such that the second area is covered by the solution. In alternative embodiments, the blocking probe is contacted to the second area in a gel form.

In some embodiments, the solution including the blocking probe can include a ligase. Non-limiting examples of suitable ligases include Tth DNA ligase, Taq DNA ligase, *Thermococcus* sp. (strain 9oN) DNA ligase (9oN™ DNA ligase, New England Biolabs), AMPLIGASE™ (available from LUCIGEN®, Middleton, Wis.), and SplintR (available from New ENGLAND BIOLABS®, Ipswich, Mass.).

In some embodiments, the concentration of the blocking probe in the solution is at least about 0.01 µM to about 50 µM, (e.g., about 0.01 µM to about 45 µM, about 0.01 µM to about 40 µM, about 0.01 µM to about 35 µM, about 0.01 µM to about 30 µM, about 0.01 µM to about 25 µM, about 0.01 µM to about 20 µM, about 0.01 µM to about 15 about 0.01 µM to about 10 about 0.01 µM to about 5 about 0.01 µM to about 2 about 0.01 to about 1 about 0.01 µM to about 0.5 about 0.01 µM to about 0.2 about 0.01 µM to about 0.1 about 0.1 µM to about 50 about 0.1 µM to about 45 about 0.1 µM to about 40 about 0.1 µM to about 35 about 0.1 µM to about 30 about 0.1 µM to about 25 about 0.1 µM to about 20 about 0.1 µM to about 15 about 0.1 about 0.1 µM to about 10 about 0.1 µM to about 5 about 0.1 µM to about 2 about 0.1 µM to about 1 about 0.1 µM to about 0.5 about 0.1 µM to about 0.2 about 0.2 to about 50 about 0.2 µM to about 45 about 0.2 µM to about 40 about 0.2 to about 35 about 0.2 µM to about 30 about 0.2 µM to about 25 about 0.2 to about 20 about 0.2 µM to about 15 about 0.2 µM to about 10 about 0.2 µM to about 5 about 0.2 µM to about 2 about 0.2 µM to about 1 about 0.2 to about 0.5 about 0.5 µM to about 50 about 0.5 µM to about 45 about 0.5 to about 40 about 0.5 µM to about 35 about 0.5 µM to about 30 about 0.5 µM to about 25 about 0.5 µM to about 20 about 0.5 µM to about 15 about 0.5 µM to about 10 about 0.5 µM to about 5 about 0.5 µM to about 2 about 0.5 µM to about 1 about 1 µM to about 50 about 1 µM to about 45 about 1 µM to about about 1 µM to about 35 about 1 µM to about 30 about 1 µM to about 25 about 1 µM to about 20 about 1 µM to about 15 about 1 µM to about 10 about 1 µM to about 5 about 1 µM to about 2 about 2 µM to about 50 about 2 to about 45 about 2 µM to about 40 about 2 µM to about 35 about 2 µM to about 30 about 2 µM to about 25 about 2 µM to about 20 about 2 µM to about 10 about 2 µM to about 5 about 5 µM to about 50 about 5 µM to about 45 about 5 µM to about 40 about 5 µM to about 35 about 5 µM to about 30 about 5 µM to about 25 about 5 µM to about 20 about 5 to about 15 about 5 µM to about 10 about 10 µM to about 50 about 10 µM to about 45 about 10 µM to about 40 about 10 µM to about 35 about 10 µM to about 30 about 10 µM to about 25 about 10 µM to about 20 about 10 µM to about 15 about 15 µM to about 50 about 15 µM to about 45 about 15 µM to about 40 about 15 µM to about 35 about 15 µM to about 30 about 15 µM to about 25 µM, about 15 µM to about 20 µM, about 20 µM to about 50 µM, about 20 µM to about 45 µM, about 20 µM to about 40 µM, about 20 µM to about 35 µM, about 20 µM to about 30 µM, about 20 µM to about 25 µM, about 25 µM to about 50 µM, about 25 µM to about 45 µM, about 25 µM to about 40 µM, about 25 µM to about 35 µM, about 25 µM to about 30 µM, about 30 µM to about 50 µM, about 30 µM to about 45 µM, about 30 µM to about 40 µM, about 30 µM to about 35 µM, about 35 µM to about 50 µM, about 35 µM to about 45 µM, about 35 µM to about 40 µM, about 40 µM to about 50 µM, about 40 µM to about 45 µM, or about 45 µM to about 50 µM).

In some embodiments, the second area of the array can be contacted by the solution for, e.g., about 5 minutes to about 1 hour, about 5 minutes to about 50 minutes, about 5 minutes to about 40 minutes, about 5 minutes to about 30 minutes, about 5 minutes to about 20 minutes, about 5 minutes to about 10 minutes, about 10 minutes to about 1 hour, about 10 minutes to about 50 minutes, about 10 minutes to about 40 minutes, about 10 minutes to about 30 minutes, about 10 minutes to about 20 minutes, about 20 minutes to about 1 hour, about 20 minutes to about 50 minutes, about 20 minutes to about 40 minutes, about 20 minutes to about 30 minutes, about 30 minutes to about 1 hour, about 30 minutes to about 50 minutes, about 30 minutes to about 40 minutes, about 40 minutes to about 1 hour, about 40 minutes to about 50 minutes, or about 50 minutes to about 1 hour, at a temperature of about 4° C. to about 35° C., about 4° C. to about 30° C., about 4° C. to about 25° C., about 4° C. to about 20° C., about 4° C. to about 15° C., about 4° C. to about 10° C., about 10° C. to about 35° C., about 10° C. to about 30° C., about 10° C. to about 25° C., about 10° C. to about 20° C., about 10° C. to about 15° C., about 15° C. to about 35° C., about 15° C. to about 30° C., about 15° C. to about 25° C., about 15° C. to about 20° C., about 20° C. to about 35° C., about 20° C. to about 30° C., about 20° C. to about 25° C., about 25° C. to about 35° C., about 25° C. to about 30° C., or about 30° C. to about 35° C.

Removing the Blocking Probe from the Second Area of the Array

In some embodiments, the solution comprising one or more blocking probes is removed by pipetting. In some embodiments, the blocking probe is removed by wicking (e.g., by an absorption paper). In some embodiments, the blocking probe is removed by washing (e.g., using a wash buffer). In some embodiments, a wash buffer can be added to contact the first and/or second area of the array then removed by pipetting, wicking, or other methods known in the art. In some embodiments, a combination of removing methods can be used. In some embodiments, contacting and removing steps can be repeated (e.g., at least 2 times, 3 times, 4 times, or greater). In some embodiments, a drying step can be performed after washing (e.g., air dry).

In some embodiments, the wash buffer is added automatically (e.g., by a robot) or manually (e.g., by pipetting). In some embodiments, the wash buffer is added vertically above the array. In some embodiments, the wash buffer is added vertically above the second area of the array. In some embodiments, the wash buffer is added dropwise by a pipette. In some embodiments, the wash buffer is added to contact all or a portion of the second area of the array. In some embodiments, the wash buffer is added to all or a portion of a surface of the non-permeabilized biological sample that is not facing or contacting the array. In some embodiments, a wash buffer is added to the whole array including the first and second areas. In some embodiments, the washing buffer is 1× TE buffer, 1× TAE buffer, 1× TBE buffer, or PBS. In some embodiments, the wash buffer contains a buffer (e.g., Tris, MOPS, HEPES, IVIES, or any other buffer known in the art), chelating agents (e.g., ethylenediaminetetraacetic acid (EDTA)), and/or metal ions (e.g., $Mg^{2+}$). In some embodiments, the wash buffer can have a pH that is about 5.0, about 5.5, about 6.0, about 6.5, about 7.0, about 7.5, about 8.0, about 8.5, about 9.0, about 9.5, or about 10.0, or about 5.0 to 5.5, about 5.5 to 6.0, about 6.0 to 6.5, about 6.5 to 7.0, about 7.0 to 7.5, about 7.5 to 8.0, about 8.0 to 8.5, about 8.5 to 9.0, about 9.0 to 9.5, or about 9.5 to 10.0.

In some embodiments, the second area of the array is contacted by the wash buffer for about 5 seconds to about 1 hour, about 5 seconds to about 50 minutes, about 5 seconds to about 40 minutes, about 5 seconds to about 30 minutes, about 5 seconds to about 20 minutes, about 5 seconds to about 10 minutes, about 5 seconds to about 5 minutes, about 5 seconds to about 1 minute, about 5 seconds to about 30 seconds, about 5 seconds to about 10 seconds, about 10 seconds to about 1 hour, about 10 seconds to about 50 minutes, about 10 seconds to about 40 minutes, about 10 seconds to about 30 minutes, about 10 seconds to about 20 minutes, about 10 seconds to about 10 minutes, about 10 seconds to about 5 minutes, about 10 seconds to about 1 minute, about 10 seconds to about 30 seconds, about 30 seconds to about 1 hour, about 30 seconds to about 50 minutes, about 30 seconds to about 40 minutes, about 30 seconds to about 30 minutes, about 30 seconds to about 20 minutes, about 30 seconds to about 10 minutes, about 30 seconds to about 5 minutes, about 30 seconds to about 1 minute, about 1 minute to about 1 hour, about 1 minute to about 50 minutes, about 1 minute to about 40 minutes, about 1 minute to about 30 minutes, about 1 minute to about 20 minutes, about 1 minute to about 10 minutes, about 1 minute to about 5 minutes, about 5 minutes to about 1 hour, about 5 minutes to about 50 minutes, about 5 minutes to about 40 minutes, about 5 minutes to about 30 minutes, about 5 minutes to about 20 minutes, about 5 minutes to about 10 minutes, about 10 minutes to about 1 hour, about 10 minutes to about 50 minutes, about 10 minutes to about 40 minutes, about 10 minutes to about 30 minutes, about 10 minutes to about 20 minutes, about 20 minutes to about 1 hour, about 20 minutes to about 50 minutes, about 20 minutes to about 40 minutes, about 20 minutes to about 30 minutes, about 30 minutes to about 1 hour, about 30 minutes to about 50 minutes, about 30 minutes to about 40 minutes, about 40 minutes to about 1 hour, about 40 minutes to about 50 minutes, or about 50 minutes to about 1 hour, at a temperature of about 4° C. to about 35° C., about 4° C. to about 30° C., about 4° C. to about 25° C., about 4° C. to about 20° C., about 4° C. to about 15° C., about 4° C. to about 10° C., about 10° C. to about 35° C. to about 10° C. to about 30° C., about 10° C. to about 25° C., about 10° C. to about 20° C., about 10° C. to about 15° C., about 15° C. to about 35° C., about 15° C. to about 30° C., about 15° C. to about 25° C., about 15° C. to about 20° C., about 20° C. to about 35° C., about 20° C. to about 30° C., about 20° to about 25° C., about 25° C. to about 35° C., about 25° C. to about 30° C., or about 30° C. to about 35° C.

In some embodiments, the solution comprising the blocking probe contains a gel precursor material (e.g., polyacrylamide) and the blocking probe is removed by first adding a solution comprising a cross-linking agent (e.g., APS/TEMED) to polymerize or gel the precursor material, followed by separating the formed gel from the second area of the array.

In some embodiments, the solution comprising the blocking probe is present as a gel, and the gel can be removed by separating the gel from the second area of the array. In some embodiments, the blocking probe is linked to a magnetic bead (or a magnetic particle, or other magnetic substance thereof) and the blocking probe can be removed by applying a magnetic field.

Figure 5:
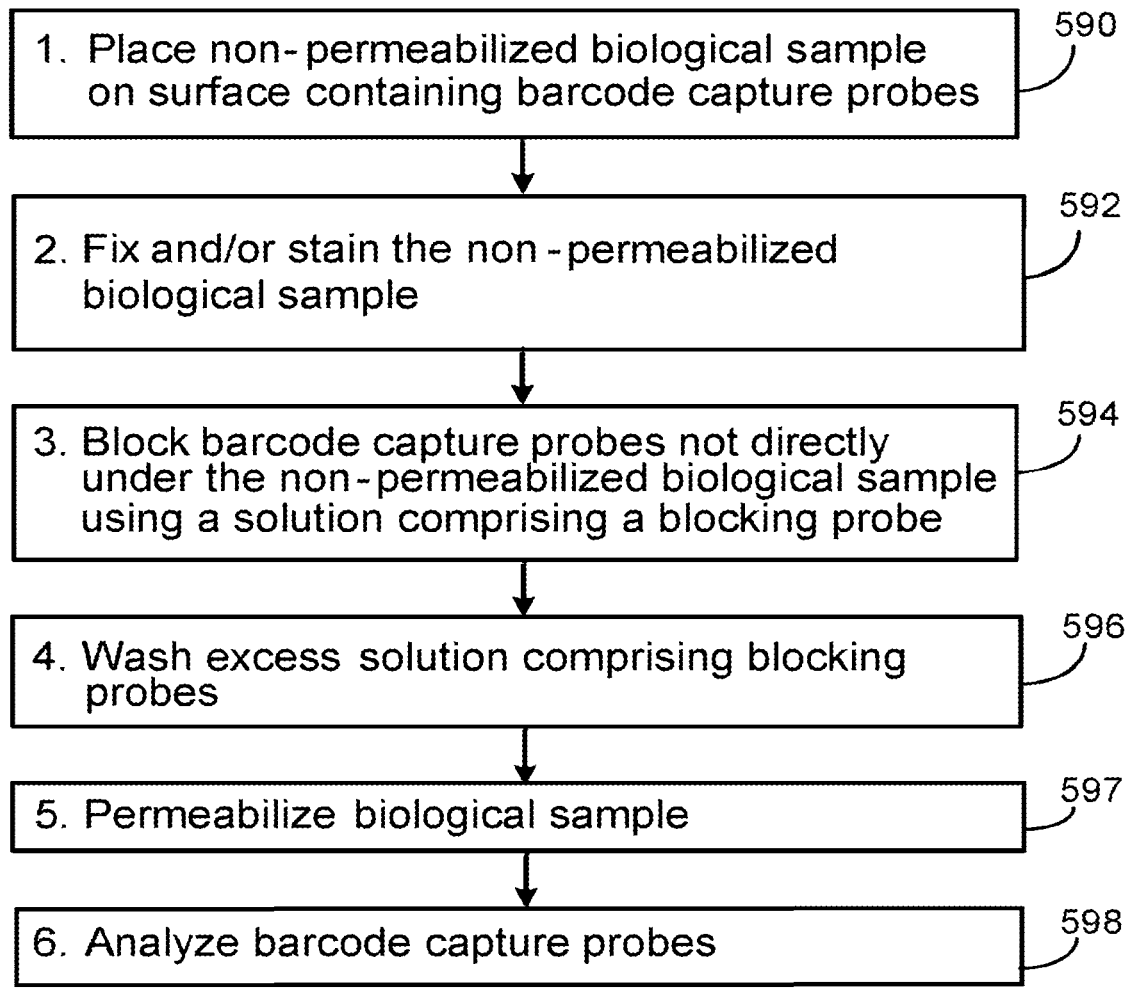
FIG. 5 shows a schematic of an exemplary workflow utilizing an exemplary embodiment of the methods described herein.

FIG. 5 shows a schematic of an exemplary workflow utilizing blocking probes. In step 590, the example workflow places the non-permeabilized biological sample on a first area of the array containing capture probes. In step 592, the non-permeabilized biological sample is fixed and/or stained. For example, a sample can be fixed via immersion in ethanol, methanol, acetone, formaldehyde, formalin, paraformaldehyde-Triton, glutaraldehyde, glutaraldehyde, or any combination thereof.

In some embodiments, the non-permeabilized biological sample can be stained. In some embodiments, the staining includes optical labels as described herein, including, but not limited to, fluorescent (e.g., fluorophore), radioactive (e.g., radioisotope), chemiluminescent (e.g., a chemiluminescent compound), a bioluminescent compound, calorimetric, or colorimetric detectable labels. In some embodiments, the staining includes a fluorescent antibody directed to a target analyte (e.g., cell surface or intracellular proteins) in the biological sample. In some embodiments, the staining includes an immunohistochemistry stain directed to a target analyte (e.g., cell surface or intracellular proteins) in the biological sample. In some embodiments, the staining includes a chemical stain, such as hematoxylin and eosin (H&E) or periodic acid-schiff (PAS). In some embodiments, staining the biological sample comprises the use of a biological stain including, but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof. In some embodiments, significant time (e.g., days, months, or years) can elapse between staining and/or imaging the biological sample.

In step 594, the example workflow blocks capture probes in the second area (e.g., not directly under the non-permeabilized biological sample) using a solution comprising a blocking probe. In some embodiments, the blocking probes can be ligated to the capture probes in the second area of the array (e.g., the area not directly under the biological sample).

In step 596, the workflow washes excess solution comprising blocking probes from the array. As mentioned herein, the solution comprising the blocking probes can be removed from the array using any of the exemplary methods described herein. For example, in some embodiments, the solution comprising a blocking probe is removed by pipetting. In some embodiments, the blocking probe is removed by wicking (e.g., by an absorption paper). In some embodiments, the blocking probe is removed by washing (e.g., using a wash buffer). In some embodiments, the wash buffer can be added to contact the second area of the array then removed by pipetting, wicking, or other methods known in the art.

In step 597, the example workflow permeabilized the biological sample. In general, a biological sample can be permeabilized by exposing the sample to one or more permeabilizing agents described herein.

In step 598, the example workflow describes analyte analysis which happens after the target nucleic acid is captured by the capture probes inferior to the biological sample on the array. For example, spatial analysis of the captured target nucleotides can be performed by determining (i) a sequence corresponding to the spatial barcode sequences of the capture probes in the first area, or a complement thereof, and (ii) a sequence corresponding to a nucleic acid analyte, or a complement thereof, in the first area. The determination of the sequences of (i) and (ii) allows for the determination of the spatial location of the nucleic acid analyte in the biological sample.

Kits

Also provided herein are kits that include an array (e.g., any of the arrays described herein) comprising a plurality of capture probes (e.g., any of the capture probes described herein), where a capture probe of the plurality of capture probes comprising a spatial barcode (e.g., any of the spatial barcodes described herein) and a capture domain (e.g., any of the capture domains described herein); and a solution comprising a blocking probe (e.g., any of the blocking probes described herein), where the blocking probe comprises a sequence that binds specifically to the capture domain of the capture probe.

In some embodiments, the kit can further comprise one or more fixative(s) (e.g., any of the fixatives described herein) to fix the biological sample and/or preserve the structure of the biological sample. Non-limiting examples of a fixative include ethanol, methanol, acetone, formaldehyde (e.g., 2% formaldehyde), formalin, paraformaldehyde-Triton, glutaraldehyde, or any combination thereof.

In some embodiments, the kit can further include one or more biological stain(s) (e.g., any of the biological stains as described herein). For example, the kit can further comprise eosin and hematoxylin. In other examples, the kit can include a biological stain selected from the group consisting of acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof.

In some embodiments, the kit can further comprise one or more permeabilization reagent(s) (e.g., any of the permeabilization reagents described herein). For example, the kit can include one or more permeabilization reagent(s) selected from the group consisting of an organic solvent, a cross-linking agent, a detergent, an enzyme, or any combination thereof.

In some embodiments, the kit can further include an enzyme. For example, in some embodiments, the kit can further include a reverse transcriptase. In other embodiments, the kit can further include a DNA polymerase. For example, in some embodiments, the kit can further include a terminal deoxynucleotidyl transferase. In some embodiments, the kit can further include an oligonucleotide. For example, in some embodiments, the kit can include a template switching oligonucleotide. In some embodiments, the kit can further include a second strand primer. In some embodiments, the kit can further include a fragmentation buffer and a fragmentation enzyme. In some embodiments, the kit can further include a DNA ligase. In some examples, the DNA ligase is a T4 DNA ligase or any of the other exemplary DNA ligases described herein. In some embodiments, the kit can further include one or more adaptors. In some examples, the one or more adaptor(s) is/are selected from the group of an i5 sample index sequence, an i7 sample index sequence, a P5 sequence platform sequence, a P7 sequence platform sequence, or any combinations thereof.

Compositions

Also provided herein are compositions comprising an array (e.g., any of the arrays described herein e.g., a bead array or a slide) having a first area (e.g., any of the first areas described herein), where the array comprises a plurality of capture probes (e.g., any of the capture probes described herein), where: the first area comprises a capture probe of the plurality of capture probes comprising a spatial barcode (e.g., any of the spatial barcodes described herein) and a capture domain (e.g., any of the capture domains described herein) specifically bound to a target analyte (e.g., any of the target analytes described herein) from the biological sample; and a second area (e.g., any of the second areas described herein) of the array comprises a capture probe of the plurality of capture probes comprising a spatial barcode and a capture domain specifically bound to a blocking probe, and the second area is adjacent to the biological sample disposed on the array.

In some embodiments, the 3' end of the blocking probe is substantially complementary to about 5 to about 100 nucleotides (or any of the subranges of this range described herein) of the capture domain of the capture probe in the second area. Non-limiting examples of blocking probes include single-stranded blocking probes, and partially double-stranded blocking probes. In some examples, a 5' end of the blocking probe is phosphorylated. In some examples, the blocking probe is ligated to a 3' end of the capture probe in the second area. In some embodiments, a 3' end of the blocking probe is chemically blocked. For example, in some embodiments, the chemical block is an azidomethyl group.

In some embodiments, the blocking probe includes a hairpin structure. In some examples, the blocking probe includes a hairpin structure. In some examples, the blocking probe includes a locked nucleic acid.

In some embodiments, the biological sample is a tissue sample (e.g., a tissue section). In some embodiments, the biological sample is a clinical sample (e.g., whole blood, blood-derived products, blood cells, cultured tissue, cultured cells, a cell suspension, or any combination thereof). In some embodiments, the biological sample is an organoid, embryonic stem cells, pluripotent stem cells, or any combination thereof. Non-limiting examples of organoids include a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, a retinal organoid, or any combination thereof. In some embodiments, the biological sample includes diseased cells, fetal cells, immune cells, cellular macromolecules, organelles, extracellular polynucleotides, or any combination thereof.

In some embodiments of any of the compositions described herein, the target analyte is DNA (e.g., genomic DNA). In some embodiments of any of the compositions described herein, the target analyte is RNA (e.g., mRNA).

EMBODIMENTS

Embodiment 1 is a method for determining a location of a target nucleic acid in a biological sample, the method comprising: (a) disposing a non-permeabilized biological sample onto an array at a first area, wherein the array comprises a plurality of capture probes, wherein: the first area comprises a capture probe of the plurality of capture probes comprising a spatial barcode and a capture domain; and a second area of the array comprises a capture probe of the plurality of capture probes comprising a spatial barcode and a capture domain, and the second area is adjacent to the biological sample disposed on the array; (b) contacting the second area of the array with a solution comprising a blocking probe, wherein the blocking probe comprises a sequence that binds specifically to the capture domain of the capture probe in the second area of the array; (c) removing residual solution comprising the blocking probe from the second area of the array; (d) permeabilizing the biological sample, such that the capture domain of the capture probe of the first area of the array binds specifically to the target nucleic acid; and (e) determining (i) all or a portion of a sequence corresponding to the spatial barcode of the capture probe of the first area of the array, or a complement thereof, and (ii) all or a portion of a sequence corresponding to the target nucleic acid, or a complement thereof, and using the sequences of (i) and (ii) to determine the location of the target nucleic acid in the biological sample.

Embodiment 2 is the method of embodiment 1, wherein a 3' end of the blocking probe is substantially complementary to about 5 to 100 nucleotides of the capture domain of the capture probe in the second area.

Embodiment 3 is the method of embodiment 1 or 2, wherein the blocking probe is single-stranded.

Embodiment 4 is the method of embodiment 1 or 2, wherein the blocking probe is partially double-stranded.

Embodiment 5 is the method of any one of embodiments 1-4, wherein a 5' end of the blocking probe is phosphorylated.

Embodiment 6 is the method of embodiment 5, wherein step (b) further comprises ligating the 5' end of the blocking probe to a 3' end of the capture probe in the second area.

Embodiment 7 is the method of any one of embodiments 1-6, wherein a 3' end of the blocking probe is chemically blocked.

Embodiment 8 is the method of embodiment 7, wherein the chemical block is an azidomethyl group.

Embodiment 9 is the method of any one of embodiments 1-8, wherein the blocking probe comprises a hairpin structure.

Embodiment 10 is the method of any one of embodiments 1-9, wherein the blocking probe comprises a locked nucleic acid.

Embodiment 11 is the method of any one of embodiments 1-10, wherein the non-permeabilized biological sample is fixed and/or stained prior to step (a).

Embodiment 12 is the method of any one of embodiments 1-10, wherein the method further comprises, between steps (a) and (b), fixing and/or staining the biological sample.

Embodiment 13 is the method of embodiment 11 or 12, wherein the step of fixing the biological sample comprises the use of a fixative selected from the group consisting of ethanol, methanol, acetone, formaldehyde, paraformaldehyde-Triton, glutaraldehyde, and combinations thereof.

Embodiment 14 is the method of any one of embodiments 11-13, wherein the step of staining the biological sample comprises the use of a biological stain selected from the group consisting of: acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, and combinations thereof.

Embodiment 15 is the method of embodiment 14, wherein the step of staining the biological sample comprises the use of eosin and hematoxylin.

Embodiment 16 is the method of any one of embodiments 11-13, wherein the step of staining the biological sample comprises the use of a detectable label selected from the group consisting of a radioisotope, a fluorophore, a chemiluminescent compound, a bioluminescent compound, or a combination thereof.

Embodiment 17 is the method of any one of embodiments 1-16, wherein the biological sample is a tissue sample.

Embodiment 18 is the method of embodiment 17, wherein the tissue sample is a tissue section.

Embodiment 19 is the method of embodiment 18, wherein the tissue section is a fresh, frozen tissue section.

Embodiment 20 is the method of any one of embodiments 1-19, wherein the biological sample is a clinical sample.

Embodiment 21 is the method of embodiment 20, wherein the clinical sample is selected from the group consisting of whole blood, blood-derived products, blood cells, and combinations thereof.

Embodiment 22 is the method of embodiment 20, wherein the clinical sample is a cultured tissue.

Embodiment 23 is the method of embodiment 20, wherein the clinical sample is cultured cells.

Embodiment 24 is the method of embodiment 20, wherein the clinical sample is a cell suspension.

Embodiment 25 is the method of any one of embodiments 1-16, wherein the biological sample is an organoid, embryonic stem cells, pluripotent stem cells, and combinations thereof.

Embodiment 26 is the method of embodiment 25, wherein the organoid is selected from the group consisting of a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, a retinal organoid, and combinations thereof.

Embodiment 27 is the method any one of embodiments 1-16, wherein the biological sample includes diseased cells, fetal cells, immune cells, cellular macromolecules, organelles, extracellular polynucleotides, and combinations thereof.

Embodiment 28 is the method of any one of embodiments 1-27, wherein the removing in step (c) comprises washing.

Embodiment 29 is the method of any one of embodiments 1-28, wherein the array comprises a slide.

Embodiment 30 is the method of any one of embodiments 1-28, wherein the array is a bead array.

Embodiment 31 is the method of any one of embodiments 1-30, wherein the determining in step (e) comprises sequencing (i) all or a portion of the sequence corresponding to the spatial barcode of the capture probe of the first area of the array, or a complement thereof, and (ii) all or a portion of the sequence corresponding to the target nucleic acid, or a complement thereof.

Embodiment 32 is the method of embodiment 31, wherein the sequencing is high throughput sequencing.

Embodiment 33 is the method of any one of embodiments 1-32, wherein the determining in step (e) comprises extending a 3' end of the capture probe of the first area of the array using the target nucleic acid as a template.

Embodiment 34 is the method of any one of embodiments 1-33, wherein the target analyte is DNA.

Embodiment 35 is the method of embodiment 34, wherein the DNA is genomic DNA.

Embodiment 36 is the method of any one of embodiments 1-33, wherein the target analyte is RNA.

Embodiment 37 is the method of embodiment 36, wherein the RNA is mRNA.

Embodiment 38 is the method of any one of embodiments 1-37, wherein the method further comprises imaging the biological sample after step (a).

Embodiment 39 is a method for determining a location of a target analyte in a biological sample, the method comprising: (a) disposing a non-permeabilized biological sample onto an array at a first area, wherein the array comprises a plurality of capture probes, wherein: the first area comprises a capture probe of the plurality of capture probes comprising a spatial barcode and a capture domain that binds specifically to the analyte capture sequence; and a second area comprises a capture probe of the plurality of capture probes comprising a spatial barcode and a capture domain, the second area of which is adjacent to the biological sample disposed on the array; (b) contacting a plurality of analyte capture agents with the non-permeabilized biological sample, wherein an analyte capture agent of the plurality of analyte capture agents comprises an analyte binding moiety barcode, an analyte capture sequence, and an analyte binding moiety that binds specifically to the target analyte; (c) contacting the second area of the array with a solution comprising a blocking probe, wherein the blocking probe comprises a sequence that binds specifically to the capture domain of the capture probe in the second area of the array; (d) removing residual solution comprising the blocking probe from the second area of the array; (e) permeabilizing the biological sample, such that the capture domain of the capture probe of the first area of the array binds specifically to the analyte capture sequence; and (f) determining (i) all or a portion of a sequence corresponding to the spatial barcode of the capture probe in the first area of the array, or a complement thereof, and (ii) all or a portion of a sequence corresponding to the analyte binding moiety barcode, or a complement thereof, and using the sequences of (i) and (ii) to determine the location of the target analyte in the biological sample.

Embodiment 40 is the method of embodiment 39, wherein a 3' end of the blocking probe is substantially complementary to about 5 to 100 nucleotides of the capture domain of the capture probe in the second area.

Embodiment 41 is the method of embodiment 39 or 40, wherein the blocking probe is single-stranded.

Embodiment 42 is the method of embodiment 39 or 40, wherein the blocking probe is partially double-stranded.

Embodiment 43 is the method of any one of embodiments 39-42, wherein a 5' end of the blocking probe is phosphorylated.

Embodiment 44 is the method of embodiment 43, wherein step (c) further comprises ligating the 5' end of the blocking probe to a 3' end of the capture probe in the second area.

Embodiment 45 is the method of any one of embodiments 39-44, wherein a 3' end of the blocking probe is chemically blocked.

Embodiment 46 is the method of embodiment 45, wherein the chemical block is an azidomethyl group.

Embodiment 47 is the method of any one of embodiments 39-46, wherein the blocking probe comprises a hairpin structure.

Embodiment 48 is the method of any one of embodiments 39-47, wherein the blocking probe comprises a locked nucleic acid.

Embodiment 49 is the method of any one of embodiments 39-48, wherein the biological sample is fixed and/or stained prior to step (a).

Embodiment 50 is the method of any one of embodiments 39-48, wherein the method further comprises, between steps (b) and (c), fixing and/or staining the biological sample.

Embodiment 51 is the method of embodiment 49 or 50, wherein the step of fixing the biological sample comprises the use of a fixative selected from the group consisting of ethanol, methanol, acetone, formaldehyde, paraformaldehyde-Triton, glutaraldehyde, and combinations thereof.

Embodiment 52 is the method of any one of embodiments 49-51, wherein the step of staining the biological sample comprises the use of a biological stain selected from the group consisting of: acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, and combinations thereof.

Embodiment 53 is the method of embodiment 52, wherein the step of staining the biological sample comprises the use of eosin and hematoxylin.

Embodiment 54 is the method of any one of embodiments 49-53, wherein the step of staining the biological sample comprises the use of a detectable label selected from the group consisting of a radioisotope, a fluorophore, a chemiluminescent compound, a bioluminescent compound, or a combination thereof.

Embodiment 55 is the method of any one of embodiments 39-54, wherein the biological sample is a tissue sample.

Embodiment 56 is the method of embodiment 55, wherein the tissue sample is a tissue section.

Embodiment 57 is the method of embodiment 56, wherein the tissue section is a fresh, frozen tissue section.

Embodiment 58 is the method of any one of embodiments 39-54, wherein the biological sample is a clinical sample.

Embodiment 59 is the method of embodiment 58, wherein the clinical sample is selected from the group consisting of whole blood, blood-derived products, blood cells, and combinations thereof.

Embodiment 60 is the method of embodiment 58, wherein the clinical sample is a cultured tissue.

Embodiment 61 is the method of embodiment 58, wherein the clinical sample is cultured cells.

Embodiment 62 is the method of embodiment 58, wherein the clinical sample is a cell suspension.

Embodiment 63 is the method of any one of embodiments 39-54, wherein the biological sample is an organoid, embryonic stem cells, pluripotent stem cells, and combinations thereof.

Embodiment 64 is the method of embodiment 63, wherein the organoid is selected from the group consisting of a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, a retinal organoid, and combinations thereof.

Embodiment 65 is the method any one of embodiments 39-54, wherein the biological sample includes diseased cells, fetal cells, immune cells, cellular macromolecules, organelles, extracellular polynucleotides, and combinations thereof.

Embodiment 66 is the method of any one of embodiments 39-65, wherein the removing in step (d) comprises washing.

Embodiment 67 is the method of any one of embodiments 39-66, wherein the array comprises a slide.

Embodiment 68 is the method of any one of embodiments 39-66, wherein the array is a bead array.

Embodiment 69 is the method of any one of embodiments 39-68, wherein the determining in step (f) comprises sequencing (i) all or a portion of the sequence corresponding to the spatial barcode of the capture probe in the first area of the array, or a complement thereof, and (ii) all or a portion of the sequence corresponding to the analyte binding moiety barcode, or a complement thereof.

Embodiment 70 is the method of embodiment 69, wherein the sequencing is high throughput sequencing.

Embodiment 71 is the method of any one of embodiments 39-70, wherein the determining in step (f) comprises extending a 3' end of the capture probe of the first area of the array using the analyte binding moiety barcode as a template.

Embodiment 72 is the method of any one of embodiments 39-71, wherein the target analyte is a protein.

Embodiment 73 is the method of embodiment 72, wherein the protein is an intracellular protein.

Embodiment 74 is the method of embodiment 72, wherein the protein is an extracellular protein.

Embodiment 75 is the method of any one of embodiments 72-74, wherein the analyte binding moiety is an antibody or an antigen-binding moiety thereof.

Embodiment 76 is the method of any one of embodiments 39-75, wherein steps (a) and (b) are performed at substantially the same time.

Embodiment 77 is the method of any one of embodiments 39-75, wherein step (a) is performed before step (b).

Embodiment 78 is the method of any one of embodiments 39-75, wherein step (b) is performed before step (a).

Embodiment 79 is the method of any one of embodiments 39-78, wherein the method further comprises imaging the biological sample after step (b).

Embodiment 80 is a kit comprising: an array comprising a plurality of capture probes, wherein a capture probe of the plurality of capture probes comprises a spatial barcode and a capture domain; and a solution comprising a blocking probe, wherein the blocking probe comprises a sequence that binds specifically to the capture domain of the capture probe.

Embodiment 81 is the kit of embodiment 80, further comprising one or more fixative(s).

Embodiment 82 is the kit of embodiment 80 or 81, further comprising one or more biological stains.

Embodiment 83 is the kit of embodiment 82, wherein the one or more biological stains comprises hematoxylin and eosin.

Embodiment 84. The kit of any one of embodiments 80-83, further comprising one or more permeabilization reagent(s).

Embodiment 85. The kit of embodiment 84, wherein the one or more permeabilization reagent(s) is selected from the group consisting of an organic solvent, a cross-linking agent, a detergent, an enzyme, and combinations thereof.

Embodiment 86 is the kit of any one of embodiments 80-85, further comprising a reverse transcriptase.

Embodiment 87 is the kit of any one of embodiments 80-86, further comprising a terminal deoxynucleotidyl transferase.

Embodiment 88 is the kit of any one of embodiments 80-87, further comprising a template switching oligonucleotide.

Embodiment 89 is the kit of any one of embodiments 80-88, further comprising a DNA polymerase.

Embodiment 90 is the kit of any one of embodiments 80-89, further comprising a second strand primer.

Embodiment 91 is the kit of any one of embodiments 80-90, further comprising a fragmentation buffer and a fragmentation enzyme.

Embodiment 92 is the kit of any one of embodiments 80-91, further comprising a DNA ligase.

Embodiment 93 is the kit of embodiment 92, wherein the DNA ligase is a T4 DNA ligase.

Embodiment 94 is the kit of any one of embodiments 80-93, further comprising one or more adaptor(s).

Embodiment 95 is the kit of embodiment 94, wherein the one or more adaptor(s) is/are selected from the group consisting of an i5 sample index sequence, an i7 sample index sequence, a P5 sample index sequence, a P7 sample index sequence, and combinations thereof.

Embodiment 96 is a composition comprising an array having a first area, wherein the array comprises a plurality of capture probes, wherein: the first area comprises a capture probe of the plurality of capture probes comprising a spatial barcode and a capture domain specifically bound to a target analyte from the biological sample; and a second area of the array comprises a capture probe of the plurality of capture probes comprising a spatial barcode and a capture domain specifically bound to a blocking probe, and the second area is adjacent to the biological sample disposed on the array.

Embodiment 97 is the composition of embodiment 96, wherein a 3' end of the blocking probe is substantially complementary to about 5 to 100 nucleotides of the capture domain of the capture probe in the second area.

Embodiment 98 is the composition of embodiment 96 or 97, wherein the blocking probe is single-stranded.

Embodiment 99 is the composition of embodiment 96 or 97, wherein the blocking probe is partially double-stranded.

Embodiment 100 is the composition of any one of embodiments 96-99, wherein the blocking probe is ligated to a 3' end of the capture probe in the second area.

Embodiment 101 is the composition of any one of embodiments 96-100, wherein a 3' end of the blocking probe is chemically blocked.

Embodiment 102 is the composition of embodiment 101, wherein the chemical block is an azidomethyl group.

Embodiment 103 is the composition of any one of embodiments 96-102, wherein the blocking probe comprises a hairpin structure.

Embodiment 104 is the composition of any one of embodiments 96-103, wherein the blocking probe comprises a locked nucleic acid.

Embodiment 105 is the composition of any one of embodiments 96-104, wherein a biological sample is disposed on the first area of the array.

Embodiment 106 is the method of embodiment 105, wherein the biological sample is a tissue sample.

Embodiment 107 is the composition of embodiment 106, wherein the tissue sample is a tissue section.

Embodiment 108 is the composition of any one of embodiments 105-107, wherein the biological sample is a clinical sample.

Embodiment 109 is the composition of embodiment 108, wherein the clinical sample is selected from the group consisting of whole blood, blood-derived products, blood cells, and combinations thereof.

Embodiment 110 is the composition of embodiment 108, wherein the clinical sample is a cultured tissue.

Embodiment 111 is the composition of embodiment 108, wherein the clinical sample is cultured cells.

Embodiment 112 is the composition of embodiment 108, wherein the clinical sample is a cell suspension.

Embodiment 113 is the composition of any one of embodiments 105-107, wherein the biological sample is an organoid, embryonic stem cells, pluripotent stem cells, and combinations thereof.

Embodiment 114 is the composition of embodiment 113, wherein the organoid is selected from the group consisting of a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, a retinal organoid, and combinations thereof.

Embodiment 115 is the composition any one of embodiments 105-107, wherein the biological sample includes diseased cells, fetal cells, immune cells, cellular macromolecules, organelles, extracellular polynucleotides, and combinations thereof.

Embodiment 116 is the composition of any one of embodiments 96-115, wherein the array comprises a slide.

Embodiment 117 is the composition of any one of embodiments 96-115, wherein the array is a bead array.

Embodiment 118 is the composition of any one of embodiments 96-117, wherein the target analyte is DNA.

Embodiment 119 is the composition of embodiment 118, wherein the DNA is genomic DNA.

Embodiment 120 is the composition of any one of embodiments 96-117, wherein the target analyte is RNA.

Embodiment 121 is the composition of embodiment 120, wherein the RNA is mRNA.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing capture of a target nucleic acid in an area of an array not covered by a biological sample, the method comprising:
   (a) disposing a biological sample onto an array at a first area, wherein the array comprises a plurality of capture probes and the biological sample is a non-permeabilized biological sample, wherein:
   the first area comprises a capture probe of the plurality of capture probes comprising (i) a spatial barcode and (ii) a capture domain; and
   a second area of the array comprises a capture probe of the plurality of capture probes comprising (i) a spatial barcode and (ii) a capture domain, and the second area is an area of the array not covered by the biological sample disposed on the array;
   (b) contacting the second area of the array with a solution comprising a blocking probe, wherein the blocking probe comprises a nucleic acid sequence that binds to the capture domain of the capture probe in the second area of the array;
   (c) removing residual solution comprising the blocking probe from at least the second area of the array prior to permeabilizing the biological sample; and
   (d) permeabilizing the biological sample, such that the capture domain of the capture probe of the first area of the array binds to the target nucleic acid; thereby reducing capture of the target nucleic acid in the second area of the array not covered by the biological sample.

2. The method of claim 1, wherein a 3' end of the blocking probe is substantially complementary to about 5 to 100 nucleotides of the capture domain of the capture probe in the second area.

3. The method of claim 1, wherein the blocking probe is a single-stranded blocking probe.

4. The method of claim 1, wherein the blocking probe is a partially double-stranded blocking probe.

5. The method of claim 1, wherein a 5' end of the blocking probe is phosphorylated.

6. The method of claim 1, wherein step (b) further comprises ligating the 5' end of the blocking probe to a 3' end of the capture probe in the second area of the array.

7. The method of claim 1, wherein a 3' end of the blocking probe comprises a chemical block.

8. The method of claim 7, wherein the chemical block is an azidomethyl group.

9. The method of claim 1, wherein the blocking probe comprises a hairpin structure.

10. The method of claim 1, wherein the blocking probe comprises a locked nucleic acid.

11. The method of claim 1, wherein the method further comprises, prior to step (a) or between steps (a) and (b), fixing and/or staining the biological sample.

12. The method of claim 11, wherein the step of fixing the biological sample comprises the use of a fixative selected from the group consisting of: ethanol, methanol, acetone, formaldehyde, paraformaldehyde-Triton, glutaraldehyde, and combinations thereof.

13. The method of claim 11, wherein the step of staining the biological sample comprises:
   the use of a biological stain selected from the group consisting of: acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, and combinations thereof; or
   the use of a detectable label selected from the group consisting of: a radioisotope, a fluorophore, a chemiluminescent compound, a bioluminescent compound, and combinations thereof.

14. The method of claim 1, wherein the biological sample is selected from the group consisting of: a tissue sample, a fresh-frozen tissue section, a fixed tissue section, an organoid, embryonic stem cells, pluripotent stem cells, diseased cells, fetal cells, immune cells, cellular macromolecules, organelles, extracellular polynucleotides, and combinations thereof.

15. The method of claim 1, wherein the biological sample is a clinical sample selected from the group consisting of: whole blood, blood-derived products, blood cells, cultured tissue, cultured cells, a cell suspension, and combinations thereof.

16. The method of claim 1, wherein the removing in step (c) comprises washing.

17. The method of claim 1, wherein the target nucleic acid is genomic DNA.

18. The method of claim 1, wherein the target nucleic acid is RNA.

19. The method of claim 18, wherein the RNA is mRNA.

20. A composition, comprising an array having a first area, wherein the array comprises a plurality of capture probes, wherein:
   the first area comprises a capture probe of the plurality of capture probes comprising (i) a spatial barcode and (ii) a capture domain bound to a target nucleic acid from a biological sample, wherein the biological sample was previously disposed on the first area; and
   a second area of the array comprises a capture probe of the plurality of capture probes comprising (i) a spatial barcode and (ii) a capture domain bound to a blocking probe, and the second area was not previously covered by the biological sample.

21. The composition of claim 20, wherein a 3' end of the blocking probe is substantially complementary to about 5 to 100 nucleotides of the capture domain of the capture probe in the second area.

22. The composition of claim 20, wherein the blocking probe is ligated to a 3' end of the capture probe in the second area.

23. The composition of claim 20, wherein the array comprises one or more features, optionally wherein the one or more features comprises a bead.

24. A composition, comprising an array having a first area, wherein the array comprises a plurality of capture probes, wherein:
- the first area comprises a capture probe of the plurality of capture probes comprising (i) a spatial barcode and (ii) a capture domain bound to a target nucleic acid from a biological sample, wherein the biological sample is disposed on the first area; and
- a second area of the array comprises a capture probe of the plurality of capture probes comprising (i) a spatial barcode and (ii) a capture domain bound to a blocking probe, and the second area is not covered by the biological sample.

25. The composition of claim 24, wherein a 3' end of the blocking probe is substantially complementary to about 5 to 100 nucleotides of the capture domain of the capture probe in the second area.

26. The composition of claim 24, wherein the blocking probe is ligated to a 3' end of the capture probe in the second area.

27. The composition of claim 24, wherein the array comprises one or more features, optionally wherein the one or more features comprises a bead.

28. The method of claim 1, wherein the method further comprises:
- (e) determining (i) a sequence corresponding to the spatial barcode of the capture probe of the first area of the array, or a complement thereof, and (ii) all or a portion of a sequence corresponding to the target nucleic acid, or a complement thereof, and using the sequences of (i) and (ii) to determine the location of the target nucleic acid in the biological sample.

29. The method of claim 28, wherein the determining in step (e) comprises sequencing (i) the spatial barcode of the capture probe of the first area of the array, or a complement thereof, and (ii) all or a portion of the target nucleic acid, or a complement thereof.

30. The method of claim 28, wherein the determining in step (e) comprises extending a 3' end of the capture probe of the first area of the array using the target nucleic acid as a template.

* * * * *